United States Patent
Mizutani et al.

(10) Patent No.: US 7,416,745 B2
(45) Date of Patent: Aug. 26, 2008

(54) PREVENTIVES OR REMEDIES FOR INFECTION, ANTI-ENDOTOXIN AGENTS, VACCINE ADJUVANTS AND GROWTH PROMOTERS

(75) Inventors: Takeo Mizutani, Kanagawa (JP); Kenji Koge, Kanagawa (JP); Yukie Nagai, Kanagawa (JP); Hiroshi Murakami, Kanagawa (JP); Toshikazu Kawai, Kanagawa (JP); Jun Kashimura, Tokyo (JP); Takeo Shimizu, Tokyo (JP); Seiichi Araki, Ibaraki (JP); Mamoru Suzuki, Ibaraki (JP)

(73) Assignee: Mitsui Sugar Co. Ltd, Tokyo (JP)

( * ) Notice: Subject to any disclaimer, the term of this patent is extended or adjusted under 35 U.S.C. 154(b) by 0 days.

(21) Appl. No.: 11/555,501

(22) Filed: Nov. 1, 2006

(65) Prior Publication Data

US 2007/0128206 A1    Jun. 7, 2007

Related U.S. Application Data

(62) Division of application No. 09/806,925, filed as application No. PCT/JP99/05583 on Oct. 8, 1999, now Pat. No. 7,150,885.

(30) Foreign Application Priority Data

Oct. 9, 1998   (JP) .................................. 10-301745
Feb. 12, 1999  (JP) .................................. 11-35047

(51) Int. Cl.
    *A61K 38/00* (2006.01)
(52) U.S. Cl. ....................................... 424/725; 424/750
(58) Field of Classification Search ........................ None
    See application file for complete search history.

(56) References Cited

U.S. PATENT DOCUMENTS

| | | | |
|---|---|---|---|
| 4,540,669 A | * | 9/1985 | Bertland et al. .......... 424/231.1 |
| 4,559,229 A | * | 12/1985 | Page et al. ................ 424/215.1 |
| 4,629,627 A | | 12/1986 | Iizuka |
| 5,102,553 A | | 4/1992 | Kearney et al. |
| 5,374,316 A | | 12/1994 | Tilby |
| 5,443,650 A | | 8/1995 | Saska et al. |
| 5,454,952 A | | 10/1995 | Brewer |
| 5,482,631 A | | 1/1996 | Saska et al. |
| 5,788,812 A | | 8/1998 | Agar et al. |
| 5,965,616 A | | 10/1999 | Wang et al. |
| 7,150,885 B2 | * | 12/2006 | Araki et al. ................. 424/725 |

FOREIGN PATENT DOCUMENTS

| | | |
|---|---|---|
| EP | 0488928 A2 | 6/1992 |
| EP | 0943343 | 9/1999 |
| JP | 69023346 | 3/1966 |
| JP | 57106624 | 7/1982 |
| JP | 58020223 | 2/1984 |
| JP | 59053427 | 3/1984 |
| JP | 60054305 | 3/1985 |
| JP | 02286623 | 11/1990 |
| JP | 04066536 | 3/1992 |
| JP | 05004929 | 1/1993 |
| JP | 11098971 | 4/1999 |
| JP | 11189519 | 7/1999 |
| WO | 9802041 | 1/1998 |

OTHER PUBLICATIONS

Bueno, Jose Hamilton Ferreira, "Sugar Can Bagasse Cellulose for Pharmaceutical Use: Development of Obtention Process," Revista de Ciencias Farmaceuticals, 1992, pp. 179-193, vol. 14.

* cited by examiner

*Primary Examiner*—Ruth A Davis
(74) *Attorney, Agent, or Firm*—Knoble, Yoshida & Dunleavy LLC

(57) ABSTRACT

A preventive or remedy for infection, an anti-endotoxin agents, a vaccine adjuvants and a growth promoter each comprising a sugar cane-derived extract as an active ingredient which agent is safe to man and animals. Also presented are foods and feeds comprising these agents.

13 Claims, 6 Drawing Sheets

PREVENTIVES OR REMEDIES FOR INFECTION, ANTI-ENDOTOXIN AGENTS, VACCINE ADJUVANTS AND GROWTH PROMOTERS

CROSS-REFERENCE TO RELATED APPLICATIONS

This application is a divisional of U.S. patent application Ser. No. 09/806,925, filed on Jun. 20, 2001 now U.S. Pat. No. 7,150,885, which, in turn, is a continuation of International application no. PCT/JP99/05583, filed on Oct. 8, 1999, now expired, under 35 U.S.C. §§365(c) and 371.

BACKGROUND OF THE INVENTION

1. Field of the Invention

The present invention relates to preventives or remedies for infection, anti-endotoxin agents, vaccine adjuvants and growth promoters for man or animals.

The present invention relates also to foods or feeds to prevent or remedy infection of man or animals.

The present invention relates also to foods or feeds to prevent or remedy human or animal diseases caused by endotoxin.

The present invention relates also to foods or feeds functioning as adjuvants for vaccines for man or animals.

The present invention relates also to foods or feeds promoting human or animal growth.

2. Description of the Prior Art

Recently, various diseases or many infectious diseases of man and animals are believed to be caused by weakened immunological functions or an insufficiency of immunological functions. In man, for example, immunological functions are weakened or made insufficient by bronchial asthma, allergic disease, joint rheumatism, autoimmune disease, nutrition lesion, surgical operations, aging, cancer, transplant of organ, or conception, resulting in concurrence of infectious diseases such as infectious diseases of respiratory organs, septicemia, and infectious diseases of urinary tracts. To treat these diseases and infectious diseases, many kinds of antibiotics are administered. However, when the antibiotic is continuously administered, its efficacy becomes weaker due to development of resistant bacteria which leads to a recently closed-up problem of hospital infection. Therefore, it is desired not to depend only on antibiotics but to develop drugs or food which enforce immunological functions themselves to thereby prevent or treat infection and to decrease dosage of antibiotics.

In the livestock and fishing industries, a large scale raising or overcrowded raising is performed to raise domestic animals, poultry or cultured fish efficiently. Such raising environment causes stresses in the animals and immune insufficiency in the animals' infancy, which leads often to various kinds of infectious diseases. As a countermeasure for this, high dosages of the antibiotics for treating or preventing diseases are administered to the animals. However, such a high dosage necessitates it in return to administer more kinds or other kinds of antibiotics in order to cope with problems of residual antibiotics, increase of resistant bacteria, and diseases caused by resistant bacteria.

Generally, known preventives or remedies comprise a single component or a plurality of components having similar structures as an active ingredient which is(are) prepared by extracting, condensing or synthesizing the components. Consequently, it is apprehended that a long time or high dosage of the preventive or remedy causes side effects.

Substances activating immunity to thereby prevent infection were found, such as some of *Bacillus subtilis, Lactobacillus bifidus,* and *Clostridium*. The immunity activating effect or infection preventive effect of the followings were reported: Egg albumen (Japanese Patent Application Laid-Open No. H3-251573), a mixture of two or more selected from egg albumen, bacteria and garlic (National Publication of Translation of PCT Application No. H8-509211), one or more selected from *Rosa roxburghii*, mugwort and cabbage and a mixture thereof (JPA Laid-Open No. H6-116158), and *Glycyrrhiza* component (JPA Laid-Open No. H9-143-85).

It is known that one can use bagasse as a culture medium for fungi such as shiitake mushrooms, fomes japonicus, straw mushrooms, hackberris, and mushrooms. Also reported are an anti-virus agent of which active ingredient is an extract from basidiomycetes (JPA Laid-Open No. H2-286623, JPA Laid-Open No. H4-66536) and an anti-virus substance obtained by fractionating and purifying an aqueous extract from cultivated substances obtained by culturing shiitake fungus on a medium comprising bagasse and rice bran (JPA Laid-Open No. H5-4929).

An anti-virus agent is know which comprises active ingredient polysaccharides and cytokinin generated by basidiomysetes cultured on bagasse as a medium (JPA Laid-Open No. S55-157517). However, the same inventor later filed another patent application on an anti-animal virus agent essentially comprising both polysaccharides and water soluble lignin as active ingredients which are prepared by subjecting bagasse to enzyme activity or boiling bagasse, followed by extraction (JPA Laid-Open No. S57-106624). However, data on an agent comprising, as the active ingredients, polysaccharides with a molecular weight of from 10,000 to 50,000 and water soluble lignin with a molecular weight of from 50,000 to 100,000 prepared by subjecting bagasse to the enzyme activity and extracting it are the same as the data described in the aforesaid JPA Laid-Open No. S55-157517. There is not described datum of any anti-virus test on the components extracted by boiling and extracting bagasse. (It should be noted that abstract description about the boiling and extraction was deleted later in an invalidation appeal procedure.) Therefore, the contents of JPA Laid-Open No. S57-106624 are substantially the same as and nothing more than those of JPA Laid-Open No. S55-157517. As summarized above, basidiomycetes containing fungi such as shiitake mushrooms and fomes japonicus are known to be physiologically active and generally used in health food. Some of the extracts from these fungi cultured bagasse are known to have anti-virus effects. To extract them, mycelia of basidiomycetes, fungi, or enzymes produced thereby are necessary.

As already described above, when infectious diseases, especially those caused by bacteria, take place, antibiotics are generally administered. In these cases, especially, where the antibiotics are administered when the causal bacteria have proliferated above a certain level, all the bacteria die at once and endotoxin present in the bacteria moves to a host, which may cause endotoxin shock in the host. Besides this sudden move of the endotoxin in blood caused by the antibiotics, the bacteria or the endotoxin thereof may circulate in blood to cause septicemia or septicemia shock.

To prevent or remedy these diseases caused by endotoxin, some anti-endotoxin agents have been reported: a method of using an antibody as an anti-endotoxin agent to remedy diseases caused by endotoxin (JPA Laid-Open No. S61-500355, National Publication of Translation of PCT Application No. H4-506447, JPA Laid-Open No. H2-104534, JPA Laid-Open No. H2-134329, JPA Laid-Open No. H6-62844, and National Publication of Translation of PCT application No.

H6-501931), a method of using hirudine which is a thrombin inhibitor (JPA Laid-Open No. H6-165691), a method of using denatured C reactive protein (National Publication of Translation of PCT Application No. H7-501545), a method of using 1,4-thiazine derivatives (JPA Laid-Open No. S63-301876), a method of using heterocyclic derivatives (JPA Laid-Open No. H3-240779), a method of using an anti-endotoxin agent comprising taurine as an active ingredient (JPA Laid-Open No. H10-158158), a method of using a novel compound (JPA Laid-Open No. H5-194470).

Recently, a vaccine adjuvants attract attention as an additive to vaccine because they are considered to play an important role for enhancing antigenicity of the vaccine. Particularly, the vaccine adjuvant is indispensable for an inactivated vaccine, because expression of the effect of the vaccine is unstable.

Currently, adjuvants clinically used for man and animals are those topically used together with vaccines, for example, plant oils such as sesame oil and colza oil, mineral oils such as complete Freund's adjuvant and incomplete Freund's adjuvant, aluminum hydroxide, and aluminum sulfate.

Studies have been made on vaccine adjuvants. Usually, an adjuvant is mixed with vaccine and is injected or orally administered. Seeking for a safer and natural adjuvant effect, studies have been reported on orally administered adjuvants derived from natural products. As oral adjuvants, reported are an adjuvant for influenza virus vaccine containing Shouseiryutou as an effective ingredient (JPA Laid-Open No. H7-173069), avian oral adjuvant containing effective ingredient NaF (JPA Laid-Open No. H10-59869), and an oral adjuvant containing an effective ingredient mutant enterotoxin (National Publication of Translation of PCT application No. H10-505059) were reported. As adjuvants derived from plants, the following has been reported: a specific lipid emulsion type of adjuvant containing a fatty oil originating from a plant, polysaccharide vaccine adjuvant comprising purified and detoxicated endotoxin and trehalose dimicolate (JPA Laid-Open No. S63-22029), an adjuvant composition containing a synthetic hydrophobic lipopolysaccharide and a surfactant component originating from a plant (JPA Laid-Open No. H5-255117), vaccine containing asemannan extracted from aloe as an adjuvant (National Publication of Translation of PCT application No. H7-506565).

Also, use of detoxicated toxins such as mutated cholera toxin and mutated heat-labile toxin and cytokine IL-12 are studied (Experimental Medicine (Jikken Igaku), 17, 199(1999)).

In the livestock and fishing industries, it is desired to grow domestic animals, fish and shrimps faster for shipping them, or to raise productivity by growing weak domestic animals, fish or shellfish which are usually considered to be too small and too weak to grow to be shipped. Many studies have been made for the purpose of growing animals faster by increasing feed efficiency, of changing taste and flavor of feed to make inexpensive and less-preferred feed more effective, or of growing weak domestic animals, fish and shellfish which are usually considered to be too weak to grow to be shipped.

As a means to increase a weight of a domestic animal, the following has been reported: an additive for animal feed containing soy bean, toad venom, araliaceae, and animal gallbladder (JPA Laid-Open No. H7-313070), a method of using a mixture of beer yeast and ethanol (JPA Laid-Open No. S48-61266), a method of using an antibiotic, multhiomycin (JPA Laid-Open No. S52-54013), a method of using a titanium complex (JPA Laid-Open No. S58-76050), a method of using globulin-containing substance (JPA Laid-Open No. S61-132143), and a method of using a carbazate (JPA Laid-Open No. S61-145156).

As a method for promoting animal growth, the following has been reported: a method of using β-phenethanolamine (JPA Laid-Open No. S59-155343), a method of using an epithelial cell growth factor (JPA Laid-Open No. S62-240625), a method of using a morphorin derivative (JPA Laid-Open No. H1-6262), and a method of using forskolin (JPA Laid-Open No. H1-320956).

As a method for decreasing a feed demanding rate to thereby improve an efficiency of weight increase of domestic animals, the following has been reported: a method of using fruit-origin vinegar (JPA Laid-Open No. S48-103364), a method of using a porcine prolactin (JPA Laid-Open No. H1-230531), and a method of using a product of a bacteriolytic enzyme and protease (JPA Laid-Open No. H2-207756).

As a method of changing preference for animal food to thereby increase a weight, a method of using hexanol or hexanal was reported (JPA Laid-Open No. H7-313067).

As a method of decreasing diseases such as diarrhea to thereby promote growth and weight increase, the following has been reported: a method of using a fructoligosaccharide (JPA Laid-Open No. S60-34134), a method of using an inulooligosaccharide (JPA Laid-Open No. S61-40754), a method of using galactosyl disaccharide (JPA Laid-Open No. H4-360652), a method of using a specific polysaccharide having β-1,3-glucan as a main chain (JPA Laid-Open No. H7-50999), an agent for increasing weight and enhancing immunity comprising, as an active ingredient, bacterial cells deprived of capsules (JPA Laid-Open No. H2-11519), and a method for enhancing immunity and increasing weight using a feed containing common-purslane (JPA Laid-Open No. H6-141784).

The preventive or remedial effect, the anti-endotoxin effect, and the vaccine adjuvant effect are all related to immunity. However, their functional mechanism are different from one another, and, accordingly, all of the preventive or remedial agents cannot work as an anti-endotoxin agent or a vaccine adjuvant. The preventive or remedial effect is that against viruses or bacteria causing infectious diseases, and is different from that against endotoxin produced by bacteria. Some having a greater preventive or remedial effect for infection raise an antibody titer of a vaccine, but others may cancel the effect of a vaccine by attacking an attenuated vaccine when they coexist together with the vaccine. The anti-endotoxin effect and the vaccine adjuvant effect are different from each other both in an object to be affected and in functional mechanism. As a consequence, a natural material having all of these effects has not been reported.

Natural preventives or remedies and anti-endotoxin agents previously reported have limited uses, because they must be orally administered in a large amount in order to express effects, or they have so strong taste, smell, or flavor that, when added to food or feed in their effective amounts, they affect taste or smell of food or feed, or raise costs. Therefore, a material is desired which has taste or smell allowable to be added to a wide range of food or feed, express a preventive or remedial effect in a small dosage against infectious diseases, and is inexpensive and of natural product-origin. Most of the natural preventive or remedy agents and anti-endotoxin agents previously reported comprise a specific ingredient as an active ingredient and it is apprehended that a long term or high dosage of them causes side effects. Therefore, among natural materials which show a preventive or remedial effect for infectious diseases in a small dosage, particularly one which comprises a plurality of active ingredients and is more natural, is desired.

Vaccine adjuvants previously reported include chemical compound adjuvants, inorganic adjuvants and biological adjuvants. Those are purified compounds, inorganic materials, or detoxicated ones of enterotoxin or endotoxin produced by bacteria. These conventionally used adjuvants do not steadily express the effects and sometimes cause a side effect of producing IgE. Recently, a natural and safer adjuvant, particularly one expressing the effects via an oral administration, is desired.

Growth promoters previously reported include chemical compounds, plants or extracts therefrom, microorganisms such as yeasts, waste materials such as deoiled soy beans, and biologically active substances contained in enzymes, proteins, or cells. However, there were only a few growth promoters which were inexpensive and easily prepared from a natural source.

An object of the present invention is to provide a preventive or remedy for infection, a preventive or remedy for endotoxin shock (an anti-endotoxin agent), a vaccine adjuvant and a growth promoter, which are safe and effective to man or animals.

Another object of the present invention is to provide a food or an animal feed comprising the preventive or remedy for infection, the anti-endotoxin agent, the vaccine adjuvant or the growth promoter.

SUMMARY OF THE INVENTION

To attain aforesaid objects, the present inventors have made studies on food safe to man or animals which food can be produced at low costs and has a preventive or remedial effect for infection, an anti-endotoxin effect, a vaccine adjuvant effect or a growth promoting effect. As a result, the inventors have found that an extract obtained by treating sugar cane, which has been used as food from an ancient time, has the preventive or remedial effect against infection caused by bacteria or viruses, the anti-endotoxin effect, the vaccine adjuvant effect and the growth promoting effect to make the present invention.

Thus, the present inventions are a preventive or remedy for infections, an anti-endotoxin agent, a vaccine adjuvant, and a growth promoter each comprising a sugar cane-derived extract as an active ingredient.

Particularly, the present inventions are the preventive or remedy for infection, the anti-endotoxin agent, the vaccine adjuvant, and the growth promoter, each comprising, as an active ingredient, a fraction obtained by treating a raw material selected from the group consisting of sugar cane juice, a liquid extract from sugar cane, and sugar cane-derived molasses, in column chromatography with a fixed carrier.

The present inventions are the preventive or remedy for infection, the anti-endotoxin agent, the vaccine adjuvant, and the growth promoter, comprising, as an active ingredient, a sugar cane-derived extract obtained by extracting bagasse with water, a hydrophilic solvent or a mixture thereof.

DESCRIPTION OF THE PREFERRED EMBODIMENTS

Figure 1:
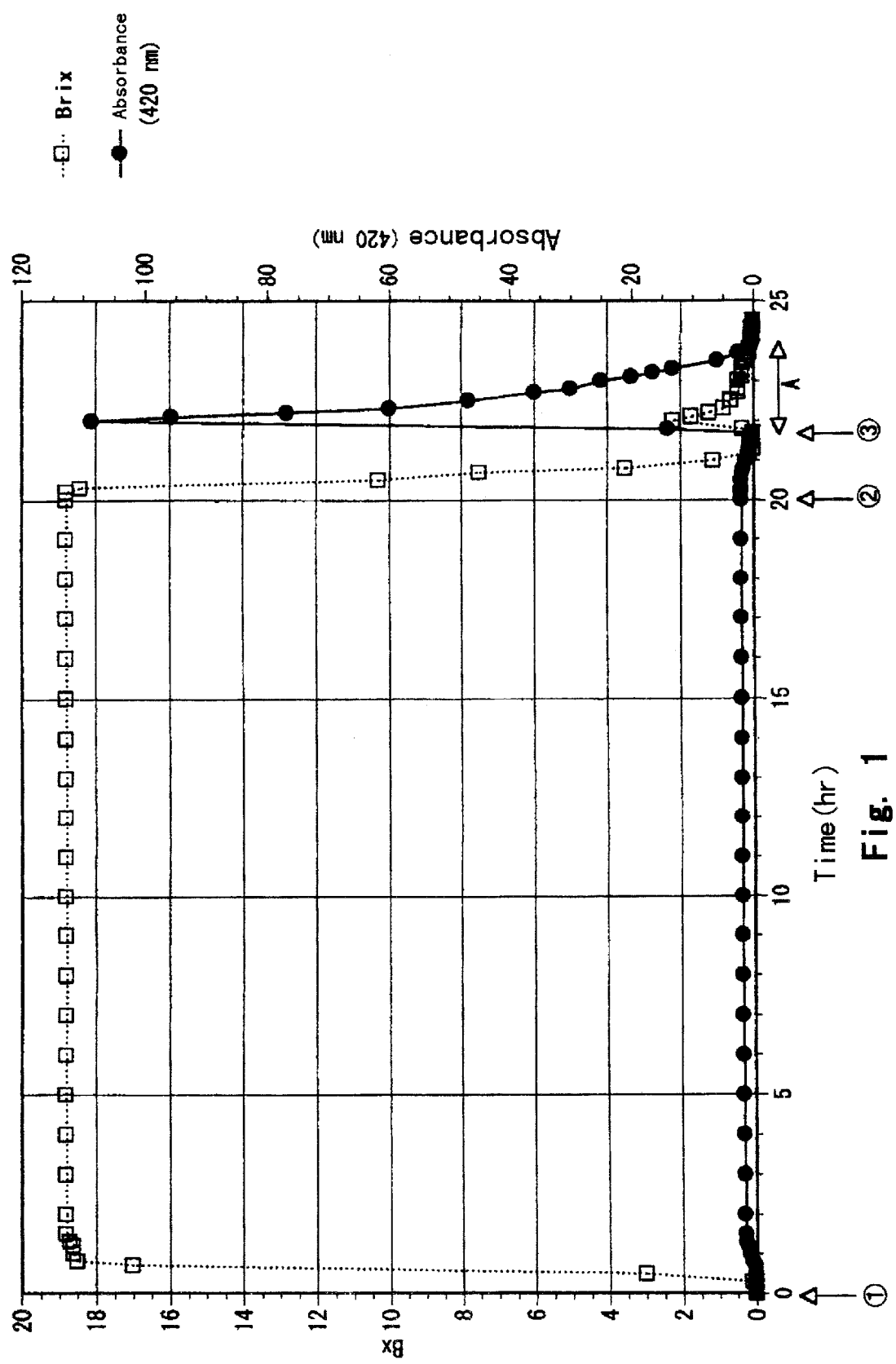
FIG. 1 shows an elution pattern obtained in column chromatography performed in Preparation Example 1.

In the specification, the terms "a preventive or remedy for infection" mean an agent having an effect of preventing or remedying infection with bacteria or viruses. Such an effect includes a preventive or remedial effect through control of immunological systems and that through other mechanisms.

In the specification, "an anti-endotoxin effect" includes a preventive or remedial effect for diseases caused by endotoxin such as an effect of decreasing death by endotoxin shock or septicemia and even an effect for oral diseases by periodontal bacteria. Further, an effect as a radical scavenger and an effect of suppressing inflammatory cytokine may be expected.

In the specification, "a vaccine adjuvant function" or "a vaccine adjuvant effect" is an effect of enhancing functions of an antigen, that is, an immune promoting effect to enhance an immune response. Specifically, it is the effect of increasing an antibody titer to thereby increase the effect of vaccination by administering the adjuvant in a specific period of time before or after vaccination.

In the specification, "a growth promoting effect" includes an effect of promoting growth of infantile man or animals and an effect of increasing body weight of thin man or animals. In the specification, the growth promoting effect is not distinguished from the weight increase-promoting effect.

In the specification, the term "animals" means vertebrates other than man, including mammals, birds and fish, for instance, domestic animals such as cows, pigs, and horses, poultry such as domestic fowls and quails, fish such as young yellowtails, sea breams, flatfish, swellfish, amberjack, sweetfish, eels, trout, carps, and goldfish, and companion animals such as dogs and cats.

In the specification, a sugar cane-derived extract is an extract obtained from sugar cane as a raw material.

In one embodiment of the invention, the sugar cane-derived extract is a fraction obtained by treating a raw material selected from the group consisting of sugar cane juice, extracted liquid from sugar cane and sugar cane-derived molasses (may be referred to simply as a raw material hereinafter) in column chromatography with a fixed carrier. More preferably, the sugar cane-derived extract is a fraction obtained by passing the raw material through a column packed with a synthetic adsorbent as the fixed carrier and eluting adsorbed substances on the synthetic adsorbent with a solvent selected from the group consisting of water, methanol, ethanol, or a mixture thereof, or a fraction which absorbs light of a wave length of 420 nm out of fractions obtained by treating the raw material in column chromatography utilizing differences in affinity to an ion exchange resin packed in a column as the fixed carrier. It is preferred to subject the fraction absorbing 420 nm light to electrodialysis to thereby decrease or, more preferably, remove salts in the fraction.

Color values of sugar cane-derived raw materials, intermediates, and products were previously evaluated absorbance at 420 nm. The absorbance at 420 nm is slightly affected by a pH of a sample, so that the pH of the sample is adjusted to about neutral pH prior to the measurement of absorbance. In the invention, absorbance is measured after adjusting samples' pH to a range of from 6 to 8. As will be described in the Examples, when 0.25 g of the freeze-dried powder of the obtained fraction is dissolved in 0.5 mM phosphate buffer (pH 7.5) to a total volume of 100 ml and its absorbance is measured at 420 nm in a cell with a path length of 1 cm, fractions having an absorbance at 420 nm of 0.8 or higher has have a higher effect of the present invention. However, the absorbance at 420 nm is a measure for content of color derived from sugar cane and it is unknown whether the absorbance at 420 nm is attributable to the present active ingredients and, further, the content of color in sugar cane vary depending on their production places and spices, so that there may not necessarily be proportional relation between the present effect and the absorbance at 420 nm among various extracts from sugar canes of different production places and spices. Therefore, absorbances at 420 nm of a plurality of fractions obtained from a raw material are measured and the fractions having a relatively higher absorbance are the fraction of the present invention.

When column chromatography is performed with a synthetic adsorbent packed in a column, active ingredients are adsorbed to the synthetic adsorbent upon passing a raw material through the column, because they have very strong affinity to the adsorbent. Subsequently, the adsorbed ingredients are desorbed and eluted with a solvent.

When an ion exchange resin is used as the fixed carrier, affinity of the present active ingredients to the resin is not so strong as adsorption. However, there is a difference of affinity to the ion exchange resin between the active ingredients and the other ingredients. Based on the difference in an eluting speed, the active ingredients can be separated from the other ingredients by feeding the raw material to the column and then passing water as an eluent.

In another embodiment of the invention, a sugar cane-derived extract is an extract obtained by extracting sugar cane-derived bagasse with a liquid selected from water, hydrophilic solvents, and a mixture thereof, more preferably, an extract obtained by extracting bagasse, which is a residue after milling sugar cane for milling juice with a liquid selected from water, hydrophilic solvents, and a mixture thereof.

In the invention, sugar cane juice includes mill juice obtained by milling sugar cane, extracted juice obtained by extracting sugar cane with water, clarified juice obtained by treating with lime in a sugar mill, and concentrated juice.

In the invention, a liquid extract of sugar cane includes an aqueous solution obtained by extracting sugar cane with a widely used organic solvent, concentrating, drying and re-dissolving in water. Examples of the organic solvent include alcohols such as methanol, ethanol and a combination thereof. A mixture of the alcohol with water may be used.

In the invention, sugar cane-derived molasses includes molasses obtained by centrifuging a mixture of sugar crystals and another liquor obtained in a crystallization process and separating molasses from the sugar crystals, such as first molasses, second molasses, final molasses in a sugar mill, and affination syrup, first to seventh molasses, and refinery final molasses in a sugar refinery. Also use is made of a residue deprived of saccharides such as an isolated liquor obtained in alcoholic fermentation of these molasses as a raw material.

In the invention, bagasse typically means bagasse exhausted in sugar manufacturing processes in a sugar mill. Here, the bagasse exhausted in sugar manufacturing processes in a sugar mill include not only a final bagasse from a final press but also finely crushed sugar cane which is bitten to be in presses of from the first press to the final press. Preferably, bagasse exhausted after milled for mill juice in the milling process in the raw sugar plant is used. The waste bagasse from the milling process varies in a moisture content, sugar content and composition depending on sugar cane species, and its harvest time. However, in the present invention, any bagasse can be used. Use is made similarly of bagasse exhausted from non-centrifugal sugar (KOKUTOU) plant, which remains after milling sugar cane. In a small scale of practice in a laboratory level, use may be made of bagasse remaining after squeezing sugar cane for press juice.

More specifically, the sugar cane-derived extract can be prepared as follows.

First, the present method of column chromatographic treatment will be explained.

Sugar cane juice, liquid extract of sugar cane obtained by extraction with a solvent or sugar cane-derived molasses (hereinafter simply referred to as a raw material) is passed through a column packed with a fixed carrier. The aforesaid raw material can be used as such or after diluted with water to a desired concentration. It is preferred to filter the raw material before treated with the column to remove any foreign substances. The filtration means is not restricted to particular one and use may be preferably made of various means widely used in the food industry such as screen filtration, diatomaceous earth filtration, precision filtration and ultrafiltration.

As the fixed carrier, a synthetic adsorbent or an ion exchange resin is preferred.

First, a preferred embodiment will be explained where a synthetic adsorbent is used as the fixed carrier. As the synthetic adsorbent, use may be preferably made of organic resins such as aromatic resins, acrylic acid type methacrylic resins and acrylonitrile aliphatic resins. More preferred are the aromatic resins, particularly unsubstituted aromatic resins. As the synthetic adsorbent, aromatic resins, for example, styrene-divinylbenzene resin may be used. As the aromatic resin, use may be made of porous resins, for example, aromatic resins having hydrophobic substituents, unsubstituted aromatic resins and porous resins such as aromatic resins obtained by subjecting unsubstituted type aromatic resins to a special treatment. More preferably, use may be made of the aromatic resins obtained by subjecting the unsubstituted type aromatic resins to a special treatment. These synthetic adsorbents are commercially available as, for example, Diaion® series, such as HP-10, HP-20, HP-21, HP-30, HP-40 and HP-50 (trade names, ex Mitsubishi Chemicals Inc.: these are unsubstituted aromatic resins), SP-825, SP-800, SP-850 and SP-875, SP-70 and SP700 (trade names, ex Mitsubishi Chemicals Inc.: these are aromatic resins obtained by subjecting the unsubstituted type aromatic resins to a special treatment); SP-900 (trade name, ex Mitsubishi Chemicals Inc., aromatic resin), Amberlight® series such as XAD-2, XAD-4, XAD-16 and XAD-2000 (trade names, ex Organo Inc.: these are aromatic resins); Diaion® series SP-205, SP-206 and SP-207 (trade names, ex Mitsubishi Chemicals Inc.: these are aromatic resins having hydrophobic substituents), HP-2MG and EX-0021 (trade names, ex Mitsubishi Chemicals Inc.: these are aromatic resins having hydrophobic substituents), Amberlight® series XAD-7 and XAD-8 (trade names, ex Organo Inc.: these are acrylic ester resins), Diaion® series HP1MG and HP2MG (trade names, ex Mitsubishi Chemicals Inc.: these are acrylic acid type methacrylic resins), Sephadex® series LH20 and LH60 (trade names, ex Pharmacia Biotech Inc.: these are cross-linked dextran derivatives) and the like. Among these, SP-850 is particularly preferable.

The amount of the fixed carrier varies depending upon a size of the column, a type of a solvent and a type of the fixed carrier. A preferable amount is 0.01 to 5 times, as a wet volume, as large as a solid content of the raw material.

Upon passing the raw material through the aforesaid column, ingredients having the present effect in the raw material are adsorbed to the carrier, and most parts of sucrose, glucose, fructose and inorganic salts pass through the column.

The ingredients adsorbed to the fixed carrier are eluted with a solvent. In order to efficiently elute the ingredients having the present effect, it is preferred to wash the column sufficiently with water to remove remaining sucrose, glucose, fructose and inorganic salts out of the column before the elution, whereby the adsorbed ingredients having intended effect are recovered efficiently. The eluting solvent is selected from water, methanol, ethanol and a mixture thereof. Preference is given to a mixed solvent of water with alcohol, particularly an ethanol-water mixture. A mixture of ethanol and water in a volume ratio of 50/50 to 60/40 is more preferred, because the ingredients having intended effects are eluted efficiently at room temperature. By elevating a column temperature, one can elute the intended ingredients having the present effect with a lower ethanol ratio in the ethanol-water mixture which can out. Here, a pressure in the column is an atmospheric pressure or higher. The ingredient having the present effect are present in the fractions eluted with the aforesaid solvent. An elution rate varies depending upon a column size, a solvent type and a type of the fixed carrier, and is not restricted to a particular rate. However, SV is preferably in the range of 0.1 to 10 hour$^{-1}$, where SV is a space velocity representing how many times a liquid volume as the resin volume is passed per hour.

The ingredients having the present effects may be obtained preferably in the following manner, but is not limited to it. That is, a raw material is passed through a column packed with an unsubstituted aromatic resin having a wet volume 0.01 to 5 times as much as a solid content of the raw material at a column temperature of 60 to 97° C. After washing the resin in the column with water, the ingredients adsorbed to the resin are eluted at a column temperature of 20 to 40° C. with a mixture of ethanol and water in a volume ratio of 50/50 to 60/40 and the fractions are collected until a volume of the eluent collected from the beginning of the elution becomes 4 times as much as the wet volume of the aforesaid resin.

Meanwhile, a preferred embodiment with an ion exchange resin as the fixed carrier will be described below. Ion exchange resins are classified into a cation exchange resin and an anion exchange resin from a viewpoint of an ion exchanging property. In the present invention, a cation exchange resin is preferably used. More preferably, a strongly acidic type, sodium ion form, or potassium ion form of cation exchange resins are used. Ion exchange resins are also classified, from a morphological viewpoint, into a gel type resin and a porous type resin such as a porous type, a macroporous type, and a highly porous type. In the present invention, a gel type ion exchange resin is preferably used. More preferably, a gel type cation exchange resin of a strongly acidic type, in a sodium ion form or in potassium ion form is used. Such ion exchange resins are commercially available, for example, include Diaion® series SK1B, SK104, SK110, SK112, SK116 (all trade names, ex Mitsubishi Chemicals Co.), UBK530, UBK550 (chromatographic grades, trade names, ex Mitsubishi Chemicals Co.), Amberlite® series Amberlite IR120B, IR120BN, IR124, XT1006, IR118, Amberlist 31, chromatographic grade Amberlite CG120, CG6000 (trade names, ex Organo Co.), Dowex® series such as HCR-S, HCR-W2, HGR-W2, Monosphere 650C, Marason C600, 50Wx2, 50Wx4, 50Wx8 (all trade names, ex Dow Chemical Japan Co.), Muromac 50WX (trade name, ex Muromachi Chemical Industry Co.), and Purolite series C-100E, C-100, C-100x10, C-120E, PCR433, PCR563K, PCR822, PCR833, PCR866, PCR883, PCR892, PCR945 (all trade names, ex AMP Ionex Co.). Among these, UBK series are particularly preferred.

The amount of the fixed carrier varies depending upon a size of column and a type of the fixed carrier. Preferably, the amount, as a wet volume, is 2 to 10,000 times, more preferably 5 to 500 times, as large as a solid content of the raw material.

The raw material is passed through the aforesaid column and then subjected to a chromatographic treatment with water as the eluent. Out of many fractions obtained, those absorbing 420 nm light are collected to obtain the intended extract. Hereinafter, this treatment method may be referred to as ion chromatographic separation.

Figure 3:
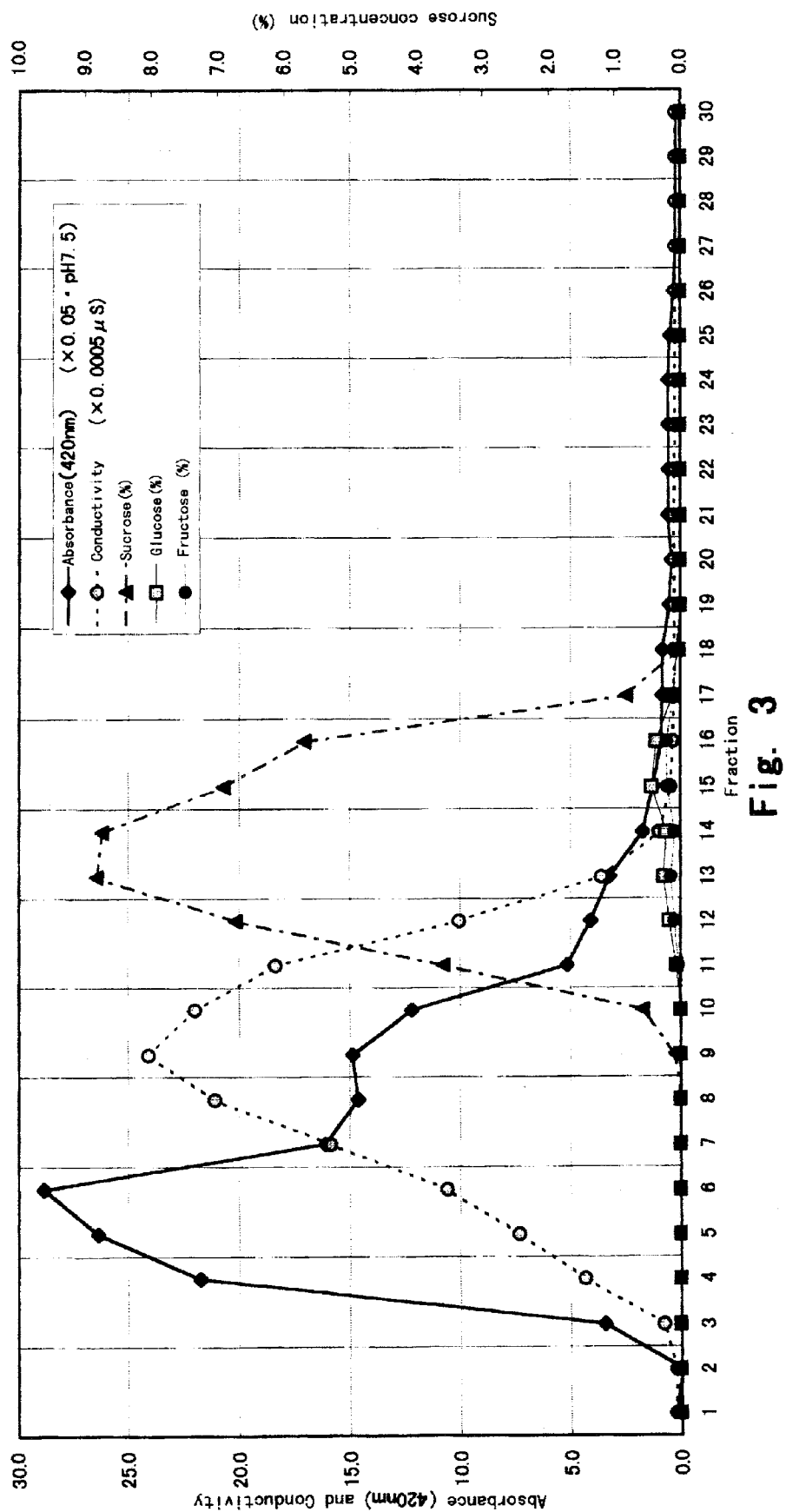
FIG. 3 shows absorbance, electric conductivity, and sugar composition of the fractions obtained by separation with an ion exchange resin performed in Preparation Example 6.

The separation conditions vary depending on composition of the raw material and a type of the fixed carrier. In a single column batch separation using degassed water as the eluent, preferred conditions are as follows: a flow rate, as SV, of from 0.3 to 1.0 hr−1, charge amount of the raw material of from 1 to 20% of a volume of the ion exchange resin, and temperature of from 40 to 70° C. For-each of the fractions obtained by this separation method, absorbance at a wave length of 420 nm, electric conductivity, which is a measure of a salt content, contents of sucrose, glucose, and fructose are determined. When these data are plotted against time, peaks in the absorbance at 420 nm, in the electric conductivity, in the sucrose content and in the content of a reducing sugar are found in this sequence. In FIG. 3, the fractions of from 3rd to 14th are collected as the fractions absorbing the light of a wave length of 420 nm. Particularly, fractions of from 3rd to 8th are preferred. The entire less-sugar fractions consisting of fractions of 1st to 9th, including fractions 3rd to 8th, and the fractions of 18th to 30th, may as well be used as the present extract, though a concentration of the active ingredients is lower. For a pseudo moving-bed continuous separation method, general separation conditions cannot be presented here because a charge rate of the raw material, a flow rate of an eluent, and a withdrawal flow rate are set according to a composition of the raw material, a type of the fixed carrier, and an amount of ion exchange resin.

The present fractions obtained by pseudo moving-bed continuous separation using a 2nd molasses from a raw sugar mill as the raw material comprise, at most 6% of sucrose and at most 90% of non-sugar component, based on a solid content, and have an apparent purity of 10%, though the composition varies depending on a type of the raw material and a separation capability of the ion exchange resin. The apparent purity is a percentage of a polarization per solid content (Brix:Bx), where polarization is an angle of rotation measured with a sucrometer relative to a pure sucrose standard of a specified concentration.

The present fractions obtained by a single column batch separation method using a 2nd molasses as the raw material contain about 5% of polyphenols, about 44.7% of electrically conductive salts and about 5% of sugar, based on a freeze-dried solid content.

It is clear that the present active ingredients are contained more in the fractions corresponding to the peak of absorbance at a wave length of 420 nm, but it has not yet been clear whether the active ingredients themselves absorb light of 420 nm.

The aforesaid fractions absorbing light at a wave length of 420 nm or the less-sugar fractions may be treated further by electrodialysis to thereby decrease or remove salts contained in the fractions. The fractions obtained by column chromatography with an ion exchange resin contain salts in an amount so much as about 40% of sulfate ash, based on a dried solid. Consequently, the fractions taste very salty and affect taste of foods. To allow man to take the fractions, the salt content should be decreased because too much intake of salts is bad for health. This applies also to animals and there is a maximum permissible salt intake. Especially for domestic animals, an amount of each kind of salt to be given is regulated, to which salt contents in a formula feed is conformed. Therefore, for application in domestic animal foods, the sugar cane-derived extract preferably contains a lower amount of the salts. Accordingly, it is preferred to decrease the salts contents of the obtained fractions.

In desalinization by electrodialysis, cations such as sodium ion, potassium ion, calcium ion, and magnesium ion are removed almost equally regardless of ion species. As to anions, it is known that chloride ion is selectively removed than sulfate ion which is not removed so well. Cation and anion are removed in an equivalent ratios.

Now, a method of preparing the sugar-cane derived extract by extracting bagasse will be explained. The bagasse extract is prepared by extracting bagasse with a solvent selected from the group consisting of water, hydrophilic solvents and a mixture thereof. Examples of the hydrophilic solvents include lower alcohols such as methanol and ethanol, ketones such as acetone, and acetates such as methyl acetate and ethyl acetate. Ethanol is a preferred hydrophilic solvent. A preferred solvent for the extraction is a mixture of ethanol and water in a volume ratio of at most 60/40, more preferably at most 50/50. For efficient extraction, an extraction temperature of from 50 to 100° C. is preferred. An extraction time is usually 1 to 3 hours, though this varies depending on bagasse's source, type, and state. Any commonly used method for extraction maybe used such as extraction in a container where bagasse and the extracting solvent are placed together, extraction by circulating the extracting solvent, continuous extraction using, for example, a Desmet extrator and a Lurgi extractor. The extract from the bagasse contains much saccharides, so that it may be subjected to column chromatograpic treatment similar to the aforesaid method to thereby remove the saccharides.

The present active ingredients may be obtained by condensing the extract from cane sugar prepared by any of the aforesaid various methods, in a conventional method such as evaporation of the solvent under vacuum and freeze-drying. The active ingredients thus obtained may be stored in a form of a condensed liquid with at least 20% of solid content or powder. Preferably, it is stored in a refrigerator, particularly when it is liquid.

As will be shown later in Test Example 4, the present sugar cane-derived extract comprises not only one active ingredient but a plurality of active ingredients and has different condensed compositions of the active ingredients depending on the method of preparation.

Preventives or remedies for infection hitherto known generally comprise a single active component or a plurality of similar active components, so that it is apprehended that a long-term or large amount of dosage would cause side effects. In contrast, the present sugar cane-derived extract comprises many components of a wide range of molecular weights and is more natural.

The present sugar cane-derived extract shows preventive or remedial effects for infection against bacteria and viruses in an animal experiment where the sugar cane-derived extract was orally administered to mice (see Examples 1 to 4). It is believed that the present sugar cane-derived extract control immunological system to thereby prevent or remedy infection.

Therefore, the present invention may be applied to prevent or remedy diseases caused by weakness or deficiency of immunological function through control of immunological function of man or animals. The present invention may be applied also to prevent or remedy various kinds of infectious disease.

Such diseases are not limited to particular ones. In the case of man, examples include articular rheumatism, glomerulonepheritis, hemolytic anemia, bronchial asthma, Behcet's disease, Hashimoto's disease, polymyositis, systemic lupus erythematosus, autoimmune diseases such as progressive systemic sclerosis and some sorts of tumors, infectious disease of a whole body, respiratory systems, urinary tracts, intestines, intra-abdomens, mucus membranes, or circulatory organs, various kinds of infectious diseases of children with nutritional disturbances, aged persons, or those who are under administration of anticancer agents or operative invasions. In the case of animals, examples include diarrhea, epidemic pneumonia and infectious gastroenteritis of pig, avian pneumonia and Marek disease, bovine diarrhea, pneumonia and mastitis, and feline immnodeficiency syndrome and leukemia. Also, infectious diseases of cultured fish are not limited to particular ones and examples include bacterial infection such as streptococcosis, pasteurellosis and virus infection.

Examples of bacterial infection include human Salmonellosis (*Salmonella enteritidis, S. dublin*), *Vibrio parahaemolyticus*, typhoid fever (*Salmonella typhi*), infectious *E. coli* infectious disease (*Escherichia coli*), tuberculosis (*Mycobacterium tuberculosis*), bacillary dysentery (*Shigella dysenteriae, S. flexneri*), pertussis (*Bordetella pertussis*), diphtheria (*Corynebacterium diphtheriae*), Hansen disease (*Mycobacterium leprae*), plague (*Yersinia pestis*), bovine mastitis (*Staphylococcus aureus, Klebsiella pneumoniae, Streptococcus agalactiae, Actinomyces pyogenes*), Brucella disease (*Brucella abortus*), Campylobacter disease (*Campylobacter fetus*), anthrax (*Bacillus anthracis*), Johne's disease (*Mycobacterium avium*), bovine infectious keratoconjuctivitis (*Moraxella bovis*), pasteurellosis (*Pasteurella multocida* and *Pasteurella haemolytica*), trichophytia interdigitalis (*Fusobacterium necrophorum*), glanders (*Bordetella mallei*), horse infectious uteritis (*Taylorella equigenitalis*), relapsing fever (*Borrelia theileri*), porcine atrophic rhinitis (*Bordetella bronchiseptica*), porcine erysipelas (*Erysipelothrix rhusiopathiae*), Glasser disease (*Haemophilus parasuis*), chicken diarrhea with white stool (*Salmonella pullorum*), domestic avian cholera (*Pasteurella multocida*), infectious coryza (*Haemophilus paragallinarum*), atypical mycobacterial disease (*Mycobacterium avium*), canine ocular leptospirosis (*Leptospira canicola*), tetanus (*Clostridium tetani*), ichthyic Enterococcus infection (*Enterococcus seriolicida*), pasteurellosis (*Pasteurella piscicida*), Vivrio disease (*Vivrio anguillarum*), Edwardsiella infection (*Edwardsiella tarda*), coldwater disease (*Flavobacterium psychrophilus*), red mouth disease (*Yersinia ruckeri*), Aeromonas infection (*Aeromonas hydrophila*), nocardiosis (*Nocardia asteroides, Nocardia seriolae*).

Examples of viral diseases include human influenza (Human influenzavirus), human herpes (Human herpesvirus 3), human immunodeficiency syndrome (Human immunodeficiency syndrome virus), poliomyelitis (Polio virus), rubella (Rubella virus), measles (Measles virus), variola (Variola virus, Japanese encephalitis (Japanese encephalitis virus), epidemic parotitis (Mumps virus), Ebola hemorrhagic fever (Ebola virus), dengue fever (Dengue virus), Marburg disease (Marburg virus), Lymphocytic choriomeningitis (Lymphocytic choriomeningitis virus), human T-lymphocyte leukemia (Human T-lymphotrophic virus), Yellow fever (Yellow fever virus), Bovine infectious rhinotracheitis (Bovine herpesvirus 1), bovine Foot-and-mouth disease (Foot-and-mouth disease virus), bovine ephemeral fever (Bovine ephemeral fever virus), Cowpox (Cowpox virus), Akaban disease (Akabane virus), Ibaraki disease (Ibaraki virus), Bluetongue (Bluetongue virus), Shipping fever (Bovine parainfluenza virus), Rift Valley fever (Rift Valley fever virus), equine infectious anemia (Equine infectious anemia virus), equine arteritis (Equine arteritis virus), Borna disease (Borna virus), equine rhinopneumonitis (Equid herpesvirus 4), easter equine encephalitis (Eastern equine encephalitis virus), porcine transmissible gastroenteritis (Porcine transmissible gastroenteritis virus), porcine reproductive and respiratory syndrome (Porcine reproductive and respiratory syndrome virus), Aujeszky's disease (Pseudorabies virus), hog cholera (Hog cholera virus), porcine vesicular disease (Swine vesicular disease virus), swine inclusion body rhinitis (Suid herpesvirus 2), avian infectious bursal disease (Infectious bursal disease virus), Newcastle disease (Newcastle disease virus), avian pox (Fowlpox virus), Marek's disease (Marek's disease virus), Infectious laryngotracheitis (Infectious laryngotracheitis virus), Avian infectious bronchitis (Avian infectious bronchitis virus), canine rabies (Rabies virus), canine distemper (Canine distemper virus), infectious hepatitis (Canine adenovirus 1), canine parvovirus infection (Canine parvovirus), Feline leukemia (Feline leukemia virus), Feline immnodeficiency syndrome (Feline immnodeficiency virus, feline infectious peritonitis (Feline infectious peritonitis virus), Feline panleukopenia (Feline panleukopenia virus), ichthyic Iridovirus infection (Flouder virus), Infectious haemotopoietic necrosis (Infectious haemotopoietic necrosis virus), infectious pancreatic necrosis (Infectious pancreatic necrosis virus), fugu white mouth disease (unidentified).

Examples of fungous diseases include human coccidioidomycosis (*Coccidioides immitis*), histoplasmosis (*Histoplasma capsulatum*), bovinemastitis (*Candida tropicalis*), miscarriage (*Aspergillus fumigatus*), dermatomycosis (*Trichophyton verrucosum*), mucormycosis (*Mucor rasemosus*), equine gluttural pouch myosis (*Aspergillus nidulans*), infectious lymphadenosis (*Histoplasma farciminosum*), equine trichophytosis (*Trichophyton equinum*), avian ingluviitis (*Candida albicans*), *Aspergillus* pneumonia (*Aspergillus fumigatus*), canine blastomycosis (*Blastomyces dermatitidis*), dermatomycosis (*Microsporum canis*), lymphadenosis (*Histoplasma capsulatum*), Malasseziasis (*Malassezia pachydermatis*), ichthyic *Saprolegnia* infection (*Saprolegnia parasitica*), visceral mycosis (*Saprolegnia diclina*), mycetogenic granuloma (*Aphanomyces piscicida*), *Pythium* infection (*Pythium gracile*), tympania (*Candida sake*).

Examples of infectious disease by mycoplasma include bovine *Mycoplasma* pneumoniae (*Mycoplasma mycoides*), *Mycoplasma* mastitis (*Mycoplasma bovis*), ovine infectious agalactia (*Mycoplasma agalactiae*), hog epidemic pneumonia (*Mycoplasma hyopneumoniae*), avian chronic upper air passage inflammation (*Mycoplasma gallisepticum*).

Examples of infectious disease by rickettsia include human typhus (*Rickettsia prowazekii*), Q fever (*Coxiella burnetii*), feline scratch disease (*Bartonella henselae*), bovine haemorrhagic fever (*Ehrlichia ondiri*), equine Potomac fever (*Ehrlichia risticii*), canine ehrlichia infection (*Ehrlichia canis*).

Examples of infectious disease by chlamydia include human psittacosis (*Chlamidia psittaci*), bovine epidemic miscarriage (*Chlamydia psittaci*), sporadic bovine encephalomyelitis (*Chlamydia pecorum*), ovine epidemic hydrohymenitis (*Chlamydia pecorum*), chlamydia hamarthritis (*Chlamydia pecorum*), feline chlamydia pneumonia (*Chlamydia psittaci*).

The present sugar cane-derived extract showed a significant increase in a survival ratio in an endotoxin model where the sugar cane-derived extract was orally administered to experimental animals one day before and 6 hours after an intravenous administration of endotoxin. This indicates that the sugar cane-derived extract itself or its metabolite acts on the endotoxin present in blood to decompose, agglomerate, or cause any change in a state of the endotoxin to neutralize it, to suppress excessive activation of complement by the endotoxin, serves as a radical scavenger, suppress inflammatory cytokine, or decreases efficiency of endotoxin through any mechanism, to thereby have anti-endotoxin effects. Therefore, the present sugar cane-derived extract can be used to prevent or remedy diseases caused by endotoxin. Such diseases are not limited to particular ones and include sepsis causing severe general symptoms such as fever, chill, vomiting and disturbance of consciousness, endotoxin shock, and oral diseases by endotoxin such as periodontal bacteria. Examples of bacterium having such endotoxin include Gram negative baterium such as *Escherichia coli* (*E. coli*), pneumobacilli, proteus, pseudomonas aeruginosa, and enterobacter.

The present sugar cane-derived extract also acts as a vaccine adjuvant and a growth promoter, as will be demonstrated in the Examples.

Administration timing of the present preventive or remedy for infection, anti-endotoxin agent, or growth promoter is not limited. The administration timing of the present vaccine adjuvant is not limited and may be before, on or after the day of administration of vaccine. Generally, it is administered on and/or after vaccination. By administrating before the vaccination, more reliable effects can be expected. At least one administration is enough and continuous or intermittent administration over a period of from one day to one week before the vaccination and from one week to two weeks after the vaccination is preferred. Further continued administration for 1 to 6 months may be made with no problem.

A Dosage of the present preventive or remedy for infection, anti-endotoxin agent, vaccine adjuvants or growth promoter is not limited and may be decided depending on purity and a form of the sugar cane-derived extract, type, health state or a stage of growth of an object animal. For example, a dosage of the sugar cane-derived extract powder prepared in Preparation Examples 1 to 7 described later in the specification is 1 to 1000 mg, preferably 50 to 1000 mg per kg body weight.

The present sugar cane-derived extract may be administered in any means such as oral, intravenous, intramuscular, subcutaneous, intracutaneous, intra-abdominal, intrarectal and hypoglossal admistraion, endermism, instillation to exert a preventive or remedial effect, anti-endotoxin effect, vaccine adjuvant effect, or growth promoting effect.

The present extract may be administered in any form. The extract in the form of liquid or powder may be administered as such or may be made into solid or liquid preparation with a carrier for preparation by a known method. Alternatively, the present extract, either prepared or not prepared, may be mixed in a food, a feed, or drinking water.

A solid preparation for oral administration may be made by adding diluent bases, binders, bonding agents, disintegrator, lubricants and brightener, colorants, flavor and odor controller, antioxidants, and dissolution aids to the present extract and making the mixture into pellets, coated pellets, granules, powder, or capsulated drugs.

The examples of the aforesaid diluent bases include starch, corn starch, dextrin, flour, wheat middling, bran, rice bran, rice bran oil cake, soybean cake, soybean powder, soybean oil cake, soybean flour, glucose, lactose, white sugar, maltose, plant oil, animal oil, hardened oil, saturated higher fatty acids, other kinds of fatty acids, yeast, mannitol, crystalline cellulose, silicon dioxide, silicic anhydride, calcium silicate, silicic acid, calcium hydrogenphosphate, calcium phosphate, and calcium dihydrogenphosphate.

Examples of the binders include polyvinylpyrrolidone, ethyl cellulose, methyl cellulose, gum arabic, tragacanth gum, hydroxypropyl cellulose, hydroxypropylmethyl cellulose, sodium alginate, sodium casein, sodium carboxymethyl cellulose, propylene glycol, and poly(sodium acrylate).

Examples of the lubricant and brightener include magnesium stearate, talc and stearic acid.

As the colorant and flavor or essence, any such agents allowed to be added to drugs, foods, or feeds may be used.

Examples of the antioxidants include ascorbic acid, α-tocopherrol, ethoxyqin, dibutylhydroxytoluene, butylhydroxyanisole and those allowed to be added to drugs, foods, or feeds. Tablets or granules may be coated as desired.

An injection medicine may be prepared by adding pH adjusting agents, buffers, suspending agents, dissolving aids, stabilizers, isotonic agents, antioxidants, preservatives and processing them by a known method. Here, the medicine may be freeze-dried medicine. Injection may be made intravenously, subcutaneously, or intramuscularly.

Examples of the suspending agents include methyl cellulose, polysolvate 80, hydroxyethyl cellulose, gum arabic, tragacanth gum powder, sodium carboxymethyl cellulose, and polyoxyethylenesorbitan monolaurate.

Examples of the dissolving aids include polyoxyethylene hardened castor oil, polysolvate 80, nicotinic amide and polyoxyethylenesorbitan monolaurate.

Examples of the preservatives include methyl paraoxybezoate, ethyl paraoxybezoate, and sorbic acid.

The present invention also relates to a food or an animal feed comprising the aforesaid preventive or remedy for infection, anti-endotoxin agent, vaccine adjuvant or growth promoter. The food or animal feed may be in a form of solid or liquid. Examples of the food include confectionery, soft drinks, functional seasoning, and health foods. Examples of the animal feed include pet foods such as dog foods and cat foods, domestic animal feeds and feeds for cultured fish and shellfish.

EXAMPLES

The present invention will be more specifically explained. The description on a dose such as "10 mg/kg" or "10 mg/kg weight" means 10 mg of a dose per kg of body weight.

Preparation Example 1

Six hundred and fifty liters of a mill juice (solid content of 18.8%) obtained in a sugar preparation process in a sugar mill were heated to 80° C. with a juice heater and then filtered through a tubular type ultrafiltration membrane (Daicel Chemical Industries Ltd., type MH-25, an effective membrane area of 2 m²×3 tubes, exclusion molecular weight of 100,000) to obtain about 600 liters of the treated juice.

Fifteen liters of a synthetic adsorbent (SP-850, trade name, ex Mitsubishi Chemical Co.) were packed in a column provided with a water jacket (column size: an inner diameter of 17.0 cm and a height of 100 cm). The aforesaid treated juice was passed through the column at a flow rate of 30 liters/hour (Space Velocity=2 hour$^{-1}$). During the passage of the filtered sugar cane juice, water at 65° C. was always circulated in the water jacket. Then, the column was washed by passing 45 liters of ion exchanged water through the column at a flow rate of 30 liters/hour (SV=2 hour$^{-1}$). After the washing with the ion exchanged water, it was confirmed that Brix of the effluent was about zero, measured by a Handref Brix meter (ex Atago Company, type N-1E). Then, an aqueous 55% ethanol solution (ethanol/water=55/45 in volume ratio) as an eluting solvent was passed through the column at a flow rate of 30 liters/hour (SV=2.0 hour$^{-1}$) to elute ingredients adsorbed to the synthetic adsorbent. During the passage of the eluting solvent, water at 25° C. was always circulated in the water jacket. The effluent from the column was collected in each portion of 5 liters. The elution pattern is as shown in FIG. 1, where (1) indicates a starting point of passing the filtered sugar cane juice; (2), a starting point of the washing with ion exchanged water; and (3), a starting point of the elution with the aqueous 55% ethanol solution. In the figure, the filled circles show absorbance at 420 nm and the empty squares show Brix of each fraction. The fraction eluded with the aqueous 55% ethanol Solution (corresponding to part "A" in FIG. 1) was condensed approximately 20 times under vacuum with a concentrator. After freeze-drying the concentrate overnight, 460 g of brown powder, i.e., sugar cane-derived extract, was obtained.

Preparation Example 2

Figure 2:
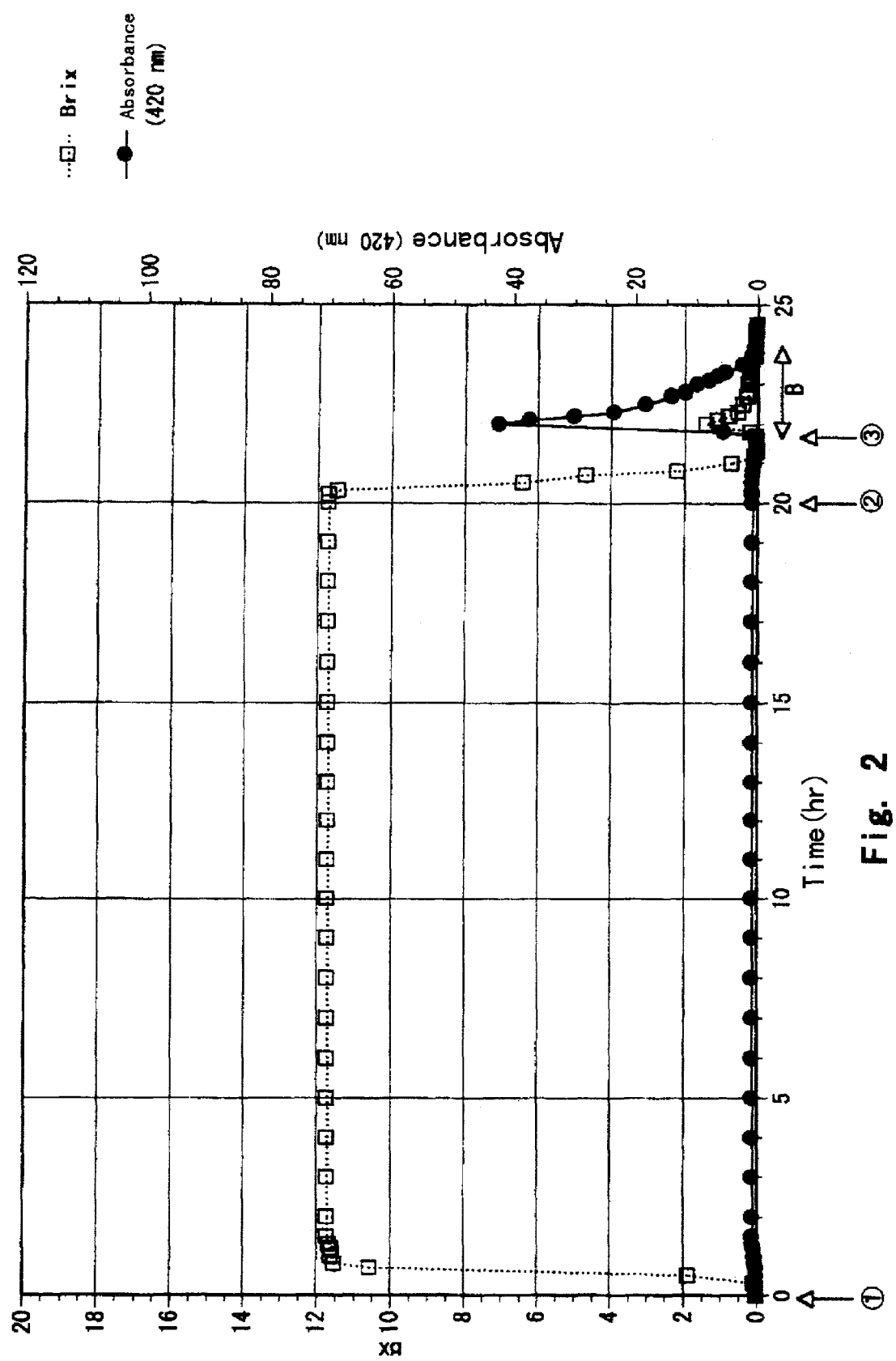
FIG. 2 shows an elution pattern obtained in column chromatography performed in Preparation Example 2.

Six hundred liters of a clarified juice (solid content of 11.7%) obtained in a sugar preparation process in a sugar mill were treated in the same manner as in Preparation Example 1 except that the juice was not treated by ultrafiltration. The elution pattern is as shown in FIG. 2, where (1) indicates a starting point of passing the clarified juice; (2), a starting point of the washing with ion exchanged water; (3), a starting point of the elution with the aqueous 55% ethanol solution. The fraction "B" in FIG. 2, was collected and condensed under vacuum. After freeze-drying the concentrate overnight, 225 g of brown powder, i.e., sugar cane-derived extract, was obtained.

Preparation Example 3

One kilogram of dried bagasse obtained in a sugar mill was put in a bag made of nylon net and the bag containing bagasse was placed in a tank, to which 25 liters of water at 80° C. was added, and extraction was carried out with stirring. After one hour extraction, the liquid extract obtained was filtered with a cotton filter to remove foreign substances. The filtrate was concentrated under vacuum with a centrifugal thin-layer concentrator. After freeze-drying the concentrate overnight, 26.31 g of dark brown powder, i.e., sugar cane-derived extract, was obtained.

Preparation Example 4

Three hundred and fifty grams of dried bagasse obtained in a sugar mill were put in a nylon net bag and placed in a tank, to which 5250 ml of an ethanol/water of a volume ratio of 50/50 was added, and extraction was carried out with stirring. After two-hour extraction, the liquid obtained was filtered with a No. 2 filter paper, ex Advantec Toyo Co., to remove foreign substances. The filtrate was concentrated under vacuum with an evaporator. After freeze-drying the concentrate overnight, 6.72 g of dark brown powder, i.e., sugar cane-derived extract, was obtained.

Preparation Example 5

Separation by Pseudo Moving-Bed Column Chromatography Using an Ion Exchange Resin A second molasses was subjected to ion exchange column chromatographic separation using a pseudo moving-bed of a cation exchange resin, which molasses had been obtained by collecting sucrose crystals twice in a boiling pan in a sugar mill and centrifuging a remaining syrup to remove crystals.

The processes from raw material preparation to ion exchange column chromatographic separation were run continuously, and the solid content and composition shown below are those measured in a steady operation, although they vary a little with time.

The second molasses had a Brix of about 85. This concentration was too high to be treated by column chromatography, so that the molasses was diluted to a Brix of about 50. To this, slaked lime and sodium carbonate were added to agglomerate impurities and then filtered through diatomaceous earth. The filtrate obtained had a Brix of 47.3, polarization of 23.6, purity of 49.9 and reducing sugar-content of 2.5%. This filtrate was subjected to ion exchange chromatography.

Ion exchange chromatography was carried out in a pseudo moving bed continuous separation method using a cation exchange resin, UBK530, ex Mitsubishi Chemical Co. The separation column packed with the resin had 8 sections, each of which contained 6.5 m$^3$ of the resin. The liquid feed and water as an eluent were continuously supplied to a different section at every predetermined time interval and a fraction containing sucrose and one containing less sucrose were taken out from different sections at every predetermined time interval. Operating conditions in a steady state were as follows: the flow rate of the feed stream was 3 m$^3$/hr; the eluent water flow rate was 13.5 m$^3$/hr; the withdrawing rate of the fraction with less sucrose was 12.13 m$^3$/hr; the withdrawing rate of the sucrose-containing fraction was 4.37 m$^3$/hr; and the switching interval was 267 seconds. By this chromatographic treatment, the sucrose-containing fraction and the fraction with less sucrose were separated from each other. The former corresponds to fractions 10 to 17 in FIG. 3, and the latter to fractions 1 to 9 and fractions 18 to 30. The sucrose-containing fraction had a sucrose content, determined by HPLC, of about 87% per solid weight and a Brix of about 35. This fraction was combined with the clarified juice and recycled to main process to recover sucrose again. The fraction with less sucrose had a sucrose content, determined by HPLC, of about 0.3% and a Brix of about 8. This fraction was condensed in a vacuum pan to a Brix of 40.0, polarization of 2.3, purity of 5.8 and reducing sugar content of 5.4%. This fraction was freeze-dried overnight to be used in further tests. Zero point twenty five gram of the freeze-dried powder obtained was dissolved in 0.5 mM phosphate buffer at pH of 7.5 a total volume of 100 ml, of which absorbance at 420 nm was determined to be 1.11.

Prepation Example 6

Fractionation of a Second Molasses by Single Column Batch Separation Using an Ion Exchange Resin A liquid prepared by treating a second molasses obtained in a sugar mill was subjected to single column batch ion chromatographic separation.

The liquid was prepared by diluting a second molasses and washing with sodium carbonate, and filtering through diatomaseous earth. This liquid raw material had a Brix of 47.4, polarization of 23.2, purity of 48.9 and a reducing sugar content of 3.2%.

This liquid raw material was subjected to fractionation by single column batch ion chromatographic separation using FPLC system (Pharmacia Co.). The column was packed with 500 ml of gel type of a strongly acidic cation exchange resin in sodium form, UBK 530, ex Mitsubishi Chemical Co. The column had an inner diameter of 26 mm and a height of 1000 mm, equipped with a flow adapter. Degassed distilled water as an eluent was passed at a flow rate of SV=0.5 hr$^{-1}$ (4.17 ml/min) at 60° C.

About 25 ml of the raw material was fed to the column. Collection of the effluent was started about 30 minutes after feeding the raw material. The effluent was collected for 3.6 min. per test tube (about 15 ml per tube), and the effluent of 30 tubes in total was recovered.

Each of the 30 fractions was analyzed for absorbance at 420 nm, electric conductivity, and sugar content. The results are as shown in FIG. 3. To measure absorbance at 420 nm, 0.1 ml of each fraction was diluted with 2 ml of 0.5 mM phosphate buffer at pH 7.5. To measure electric conductivity, each fraction was diluted with distilled water to 0.5%. A sucrose content was measured by HPLC.

To examine relationship of an anti-virus activity to each of the chromatographic peaks, the fractions corresponding to the peak of the absorbance at 420 nm were grouped into 4 samples; those corresponding to the sucrose peak into 3 samples; and those corresponding to the effluent later than the sucrose peak into 1 sample. That is, fractions 3 and 4 were combined together as sample 1; fractions 5 and 6 as sample 2; fractions 7 and 8 as sample 3; fractions 9 and 10 as sample 4; fractions 11 and 12 as sample 5; fractions 13 and 14 as sample 6; fractions 15 and 16 as sample 7; and fractions from 17 to 30 as sample 8. Fractions 1 and 2 were discarded since almost nothing was eluted. Each sample was freeze-dried overnight to become powder. Zero point twenty five gram of the freeze-dried powder obtained was dissolved in 0.5 mM phosphate buffer at pH7.5 to a total volume of 100 ml of which absorbance at 420 nm was determined. The results are as shown in Table 1. Sample 8 had a relatively high absorbance of 0.86, because it was a collection of the tail of the peak. While the samples other than sample 8 were each a mixture of two fractions, sample 8 was a mixture of 14 fractions. Therefore, sample 8 has a higher absorbance, but it is not efficient for the present purpose to collect those fractions only. In Table 1, the electric conductivity ash content was calculated from a factor determined from a correlation of electric conductivities with known sulfate ash contents.

The analytical results are as shown in Table 1. In the table, a distribution ratio of a freeze-dried solid content means a weight ratio of a solid content of each sample to a total solid content of the entire samples. The electric conductivity ash content and the content of each saccharide are ratios of those to a solid content of each sample.

Judging from each of the saccharides contents, it is seen that samples 1 to 3 correspond to a fraction with less sugar and samples 4 to 8 to a sugar-containing fraction.

TABLE 1

Analytical Data of 2nd Molasses Samples Fractionated with an Ion Exchange Resin

|  | Distribution ratio of a freeze-dried solid content (%) | Electric conductivity ash content (%) | Sucrose content (%) | Glucose content (%) | Fructose content (%) | Absorbance |
|---|---|---|---|---|---|---|
| Sample 1 | 3.1 | 32.9 | 0 | 0 | 0 | 2.72 |
| Sample 2 | 7.2 | 39.7 | 0 | 0 | 0 | 2.01 |
| Sample 3 | 10.7 | 51.4 | 10.4 | 0 | 0 | 0.83 |
| Sample 4 | 21.9 | 32.6 | 45.6 | 1.4 | 0.7 | 0.33 |
| Sample 5 | 25.9 | 18.8 | 64.2 | 2.9 | 1.3 | 0.16 |
| Sample 6 | 19.6 | 10 | 73.5 | 4.7 | 2.3 | 0.11 |
| Sample 7 | 8.4 | 3.5 | 74 | 6.2 | 3.2 | 0.14 |
| Sample 8 | 3.1 | 3.3 | 29.8 | 4.5 | 4.4 | 0.86 |
| Separated liquid by Ion chromatography | — | 43.7 | 5.9 | 0.9 | 1.4 | 1.04 |

Preparation Example 7

Desalinization of the Extract Obtained by Ion Chromatographic Separation

Using an electrodialysis bath, CH-0, ex Asahi Glass Co., provided with a cation exchange membrane, Selemion CMV, and an anion exchange membrane, Selemion AMV, both ex Asahi Glass Co., the sugar cane-derived extract(condensed liquid extract) prepared in Preparation Example 5 was desalinized by electrodialysis.

Ten liters of a 100 g/l sodium chloride solution as a condensing solution, and 4.0 liters of a 50 g/l sodium sulfate solution as an electrode solution were used. As a raw material, 10.7 liters of the ion chromatography effluent was used.

Operating conditions were as follows. An electric voltage was kept constant at 3.0V. Initially, an electric current was 8.15 A, which gradually decreased as desalinization proceeded. When 5 hours passed, the electric current was 1.6 A, 8 liters of the condensing liquid were taken out and 8 liters of water was added for dilution. Subsequently, the operation was resumed and continued for 7 hours in total. The final electric current was 0.6 A. Progress of the desalinization was monitored by measuring chloride ion and sulfate ion concentrations in the desalinized liquid with time. In the desalinization by electrodialysis, equivalent amounts of anion and cation are removed. Cations such as potassium ion, sodium ion, calcium ion, and magnesium ion are removed almost equally regardless of ion species, but anions such as chloride ion and sulfate ion are removed on a different ratio. In this Example, concentrations of chloride ion and sulfate ion per dried solid, as typical anions, were determined by HPLC and their removal ratios were calculated. At the beginning of the desalinization, a content of chloride ion per dried solid of the extract to be desalinized was 5.45 wt %, that of sulfate ion was 7.41 wt %, and that of sulfate salts was 43.0 wt %. After completion of the desalinization, a content of chloride ion per dried solid was 0.03 wt % (removal ratio of 99.4%), that of sulfate ion was 6.61 wt % (removal ratio of 10.8%), and that of sulfate salts was 34.7 wt % (removal ratio of 19.3%).

By electrodialysis, only a little quantity of sulfate ion was removed, but most of chloride ion was removed. The obtained extract was freeze-dried overnight to become powder. Zero point twenty five gram of the obtained powder was dissolved in 0.5 mM phosphate buffer at pH7.5 to a total volume of 100 ml of which absorbance at 420 nm was measured. The absorbance was 1.26.

Test Example 1

Acute Toxicity Test of Sugar Cane-Derived Extract

Using the extract powder prepared in Preparation Example 1, a toxicity test by single oral administration was carried out using rats. Sixteen male and sixteen female Sprauge-Dawley line SPF rats (Crj:CD(SD)) of 5 week-old were quarantined and fed for about a week. Healthy rats were selected and subjected to the test at 6 week-age. At the time of administration, the male rats weighed from 157 to 171 g and the female rats from 123 to 133 g. The rats were fed in an animal room lit for 12 hours at a temperature of 23+/−3° C., a relative humidity of 50+/−2%, and a ventilation frequency of 10 to 15 times per hour, in which the rats were allowed to freely intake solid food, CRF-1, trade name, ex Oriental Yeast Co., and drinking water. To the rats fasted overnight( for about 16 hours) before the day of the administration, the sugar cane-derived extract powder of a predetermined concentration was forcibly administered orally one time at 10 ml/kg body weight. To a control group, sterilized distilled water only was administered in the similar manner. Feeding was resumed 6 hours after the administration.

In addition to the control group, there were 2 groups with different dosages of 200 mg/kg and 1000 mg/kg. Thus, 3 groups in total were tested. Each group consisted of 5 males and 5 females. The results are as shown in Table 2.

TABLE 2

Toxicity Test by a Single Oral Administration

| Concentration (weight/volume %) | Administered volume (ml/kg body weight) | sex | the number of rats | the number of deaths | animal No. |
|---|---|---|---|---|---|
| 0 | 10 | male | 5 | 0/5 | 1001~1005 |
| 0 | 10 | female | 5 | 0/5 | 1101~1105 |
| 2 | 10 | male | 5 | 0/5 | 2001~2005 |

TABLE 2-continued

Toxicity Test by a Single Oral Administration

| Concentration (weight/volume %) | Administered volume (ml/kg body weight) | sex | the number of rats | the number of deaths | animal No. |
|---|---|---|---|---|---|
| 2 | 10 | female | 5 | 0/5 | 2101~2105 |
| 10 | 10 | male | 5 | 0/5 | 3001~3005 |
| 10 | 10 | female | 5 | 0/5 | 3101~3105 |

A lethal dose is estimated to be larger than 1000 mg/kg, because neither female nor male rat died 14 days after the administration of the maximum dosage of 1000 mg/kg.

During the feeding of the rats, no abnormality was observed in any of the rats. In addition, the dosed groups showed almost identical change in body weight with that of the control group, and their increase in body weight during the observation period is almost the same as that of the control group. In an anatomical examination, no rat showed abnormality in organs and tissues in the body surface, head, chest, and abdominal region.

Judging from the aforesaid results, toxicity of the extract powder obtained in Preparation Example 1 is extremely low, when the powder is orally administered to a rat one time.

Test Example 2

Antibacterial Activity of the Sugar Cane-Derived Extract Against *E. coli*

Using each of the extract powders prepared in Preparation Examples 1 to 4, minimum growth inhibiting concentrations (MIC, μg/ml) for 6 strains of *Escherichia coli* (*E. coli*) were determined according to the method specified by the Japanese Chemotherapy Association. The extract was dissolved in and diluted with sterilized distilled water to five levels of concentration of 100 μg/ml, 300 μg/ml, 1000 μg/ml, 3000 μg/ml, and 10000 μg/ml and MIC was determined. MIC was found to be 1000 μg/ml for all of the 6 strains of *E. coli*, so that no strong antibacterial activity was observed. The results are as shown in Table 3 below.

TABLE 3

Minimum Growth Inhibiting Concentration for Each of the Bacteria (μg/ml)

| Name of bacteria | Exatract in Prep. Example 1 | Exatract in Prep. Example 2 | Exatract in Prep. Example 3 | Exatract in Prep. Example 4 |
|---|---|---|---|---|
| *Escherichia coli* NIHJ | 10000 | 10000 | 10000 | 10000 |
| *Escherichia coli* C-1 | 10000 | 10000 | 10000 | 10000 |
| *Escherichia coli* C-2 | 10000 | 10000 | 10000 | 10000 |
| *Escherichia coli* C-3 | 10000 | 10000 | 10000 | 10000 |
| *Escherichia coli* TK-18A | 10000 | 10000 | 10000 | 10000 |
| *Escherichia coli* E01292 | 10000 | 10000 | 10000 | 10000 |

Similar tests were carried out for several strains of other bacteria, yeast and fungus. MICs for bacteria (*Pseudomonas aureofaciens*), yeasts (*Saccharomyces cerevisiae, Hansenula anomala*, etc.) and fungi (*Chaetomium globsum*) were 1000 μg/ml, which indicates a stronger antibacterial activity than that against *E. coli*.

Test Example 3

Proliferation-Inhibiting Property of the Sugar Cane-Derived Extract

Using each of the extract powders prepared in Preparation Examples 1 and 2, a proliferation inhibiting-property against Coxsackie virus type B6 Schmitt strain and Herpes simplex virus type 1 HF strain was examined.

At first, cytotoxicity of the extract to human embryo lung-derived cell (HEL-R66 cell) was examined. The sugar cane-derived extract was dissolved in and diluted with sterilized distilled water to a concentration of from 125 to 2000 μg/ml and applied to cultured cells. After 4 day-long culture, existence of denaturation in the cells was observed with a microscope. As shown in Table 4, no toxicity to the cells was observed up to a concentration of 1000 μg/ml.

Next, 100 PFU of viruses were inoculated to the cells. After the viruses were adsorbed to the cells, the excess viruses were removed. To a maintenance medium for the cells, the sugar cane-derived extract was added in such an amount that a final concentration of the extract was in the range of from 125 to 1000 μg/ml. The cells with the viruses adsorbed thereto were cultured for 4 days. After the cultivation, existence of proliferation of the cells was observed with a microscope. As shown in Tables 5 and 6, it was found that the sugar cane-derived extract does not have a proliferation-inhibiting effect against Coxsackie virus, while it has a proliferation-inhibiting effect against Herpes virus at a concentration of from 500 to 1000 μg/ml.

TABLE 4

Cytotoxicity

| | Final concentration of sugar cane-derived extract (μg/ml) | | | | |
|---|---|---|---|---|---|
| | 125 | 250 | 500 | 1000 | 2000 |
| Extract in Preparation Example 1 | − | − | − | − | + |
| Extract in Preparation Example 2 | − | − | − | − | + |
| Sterilized distilled water (control) | − | − | − | − | − |

TABLE 5

Proliferation Inhibiting-Property against
Coxsackie Virus Type B6 Schmitt Strain

|  | Final concentration of sugar cane-derived extract (μg/ml) | | |
|---|---|---|---|
|  | 125 | 250 | 1000 |
| Extract in Preparation Example 1 | − | − | − |
| Extract in Preparation Example 2 | − | − | − |
| Sterilized distilled water (control) | − | − | − |

TABLE 6

Proliferation Inhibiting-Property against Herpes Simplex Virus Type 1HF Strain

|  | Final concentration of sugar cane-derived extract (μg/ml) | | | |
|---|---|---|---|---|
|  | 125 | 250 | 500 | 1000 |
| Extract in Preparation Example 1 | − | − | ± | + |
| Extract in Preparation Example 2 | − | − | ± | + |
| Sterilized distilled water (control) | − | − | − | − |

Example 1

S1c:ICR male mice of 5 week-old (about 30 g in body weight) were used in 10 mice per group. Each of the extract prepared in the aforesaid Preparation Examples 1 to 4 was dissolved or suspended in sterilized distilled water. The extract solution or suspension was orally administered to the mice in an amount of 100 mg/kg or 500 mg/kg on the day before inoculation of E. coli. To a control group of the mice, the same volume of sterilized distilled water was orally administered. A suspension of man-origin E. coli was subcutaneously inoculated to the mice in an amount of 0.2 ml which corresponded to 1 minimum lethal dose, MLD, ($4.0 \times 10^7$ CFU/mouse). Four days' survival ratio was determined 4 days after the inoculation. The results were evaluated by $\chi^2$ test as shown in Table 7.

TABLE 7

Infection Preventing Test against E. coli

| Tested Exatract | Administered amount of extract | Survival ratio (%) | $\chi^2$ test |
|---|---|---|---|
| Control |  | 0 |  |
| Exatract in Preparation Example 1 | 100 mg/kg | 40 | * |
| Exatract in Preparation Example 1 | 200 mg/kg | 60 | ** |
| Exatract in Preparation Example 1 | 500 mg/kg | 80 | ** |
| Exatract in Preparation Example 2 | 100 mg/kg | 30 |  |
| Exatract in Preparation Example 2 | 500 mg/kg | 50 | * |
| Exatract in Preparation Example 3 | 100 mg/kg | 30 |  |
| Exatract in Preparation Example 3 | 200 mg/kg | 50 | * |
| Exatract in Preparation Example 3 | 500 mg/kg | 80 | ** |
| Exatract in Preventive Example 4 | 100 mg/kg | 0 |  |
| Exatract in Preventive Example 4 | 200 mg/kg | 10 |  |
| Exatract in Preventive Example 4 | 500 mg/kg | 40 | * |

* $p < 0.05$,
** $p < 0.01$

The groups which were inoculated with E. coli after the administration of the sugar cane-derived extract clearly showed higher survival ratios, which ratio increased with the increasing amount of the administration. That is, an infection preventing effect was recognized in the sugar cane-derived extract.

Example 2

1) Tested Extracts

In addition to the sugar cane-derived extracts prepared in Preparation Examples 1 to 4, the following extract was also prepared. Thus, first extract prepared in Preparation Example 2 was suspended in sterilized distilled water and dialyzed against sterilized water in a dialysis tube made of cellulose ester with a fractionating molecular weight of 1000 (Spectra/Por, tradename, cellulose ester membrane MWCO:1000, ex Spectrum Co.). The resultant liquid inside the dialysis membrane which is referred to as the fraction with a molecular weight of 1000 or more, and the liquid outside the membrane which is referred to as the fraction with a molecular weight smaller than 1000, were condensed to dryness and used for tests.

2) Anti-Virus Test

S1c:ICR male mice of 5 week-old (about 30 g in body weight) were used in 10 mice per group. Each of the extract prepared in Preparation Examples 1 to 4, the fraction with a molecular weight of 1000 or more, and the fraction with a molecular weight smaller than 1000 from Preparation Example 2 was dissolved or suspended in sterilized distilled water. The extract solution or suspension was orally or intramuscularly administered to the mice in an amount shown in Table 7. The administration was performed 3 times in total, i.e., immediately after, one day after and two days after the inoculation of virus, or 9 times in total, i.e., three times per day×3 consecutive days. To the reference group of the mice, the same volume of sterilized distilled water was orally administered. A suspension of pig-origin Pseudorabies virus was subcutaneously inoculated to the mice in an amount of 0.2 ml, which corresponded to 1 MLD (133 PFU/mouse). Seven days' survival ratio was determined. The results were evaluated by $\chi^2$ test as shown in Table 8.

TABLE 8

Infection Preventing Test against Virus

| Tested Extract | Administered amount of extract | Administration method | The number of administration | Survival ratio (%) | $\chi^2$ test |
|---|---|---|---|---|---|
| Control | | Oral | | 0 | |
| Exatract in Prep. Ex. 1 | 100 mg/kg | Oral | ×3*1 | 20 | |
| Exatract in Prep. Ex. 1 | 200 mg/kg | Oral | ×3 | 60 | ** |
| Exatract in Prep. Ex. 1 | 500 mg/kg | Oral | ×3 | 80 | ** |
| Exatract in Prep. Ex. 2 | 100 mg/kg | Oral | ×3 | 10 | |
| Exatract in Prep. Ex. 2 | 200 mg/kg | Oral | ×3 | 30 | |
| Exatract in Prep. Ex. 2 | 500 mg/kg | Oral | ×3 | 70 | ** |
| Exatract in Prep. Ex. 3 | 100 mg/kg | Oral | ×3 | 20 | |
| Exatract in Prep. Ex. 3 | 200 mg/kg | Oral | ×3 | 40 | * |
| Exatract in Prep. Ex. 3 | 500 mg/kg | Oral | ×3 | 70 | ** |
| Exatract in Prep. Ex. 4 | 100 mg/kg | Oral | ×3 | 10 | |
| Exatract in Prep. Ex. 4 | 200 mg/kg | Oral | ×3 | 30 | |
| Exatract in Prep. Ex. 4 | 500 mg/kg | Oral | ×3 | 60 | ** |
| Exatract in Prep. Ex. 2 | 25 mg/kg | Oral | ×3 × 3*2 | 0 | |
| Exatract in Prep. Ex. 2 | 50 mg/kg | Oral | ×3 × 3 | 30 | |
| Exatract in Prep. Ex. 2 | 100 mg/kg | Oral | ×3 × 3 | 40 | * |
| Exatract in Prep. Ex. 2 | 200 mg/kg | Oral | ×3 × 3 | 70 | ** |
| Exatract in Prep. Ex. 2 | 500 mg/kg | Oral | ×3 × 3 | 90 | ** |
| Exatract in Prep. Ex. 2 (Mw <1000) | 125 mg/kg | Oral | ×3 | 20 | |
| Exatract in Prep. Ex. 2 (Mw <1000) | 250 mg/kg | Oral | ×3 | 40 | * |
| Exatract in Prep. Ex. 2 (Mw <1000) | 500 mg/kg | Oral | ×3 | 80 | ** |
| Exatract in Prep. Ex. 2 (Mw >= 1000) | 500 mg/kg | Oral | ×3 | 20 | |
| Exatract in Preparation Example 2 (Mw <1000) | 1.56 mg/kg | Intramuscular | ×3 | 20 | |
| Exatract in Prep. Ex. 2 (Mw <1000) | 6.25 mg/kg | Intramuscular | ×3 | 30 | |
| Exatract in Prep. Ex. 2 (Mw <1000) | 25.0 mg/kg | Intramuscular | ×3 | 60 | ** |

\* $p < 0.05$,
\*\* $p < 0.01$
*1 Administered one time per day × 3 consecutive days.
*2 Administered three times per day × 3 consecutive days.

The groups administered the sugar cane-derived extract clearly showed higher survival ratios which increased with the increasing amount of the administration. That is, a preventive effect for infection was recognized in the sugar cane-derived extract. In the processed extract from Preparation Example 2, the fraction with a molecular weight smaller than 1000 had a higher effect than the fraction with a molecular weight of 1000 or higher. A significant survival ratio was attained by the intramuscular administration. Thus, it is found that the present sugar cane-derived extract is effective also when intramuscularly administered based on the fact that.

Example 3

Infection-Preventing Effect Against *E. coli* by an Intake of the Less-Succharaide Fraction 1) Tested Extract The extract powder prepared by ion chromatographic separation in Preparation Example 5 and the desalinized powder of extract prepared by ion chromatographic separation in Preparation Example 7 were tested.

2) Test of a Preventive Effect Against Infection by *E. coli*

S1c:ICR male mice of 5 week-old (about 30 g in body weight) were used in 10 mice per group.

Each of the aforesaid extract was dissolved or suspended in sterilized distilled water and orally administered in an amount shown in Table 9 to the mice on the day before the inoculation of *E. coli*. To the control group of the mice, the same volume of sterilized distilled water was orally administered. A suspension of man-origin *E. coli* was subcutaneously inoculated to the mice in an amount of 0.2 ml which corresponded to 1 MLD ($4.0 \times 10^7$ CFU/mouse). Four days' survival ratio was determined. The results evaluated by $\chi^2$ test are as shown in Table 9.

The groups administered the sugar cane-derived extract clearly showed higher survival rates which increased with increasing amount of the administration. No effect of desalinization was observed.

TABLE 9

Infection Preventing Test against *E. coli*

| Tested Exatract | non-sugar content (%) | Administered amount of extract mg/kg (as non-sugar) | Survival ratio (%) | $\chi^2$ test |
|---|---|---|---|---|
| Control | | Sterilized water 0.5 ml | 0 | |
| Exatract in Preparation Example 5 | 91.8 | 109 (100*[1]) | 20 | |
| Exatract in Preparation Example 5 | 91.8 | 218 (200) | 50 | * |
| Exatract in Preparation Example 5 | 91.8 | 545 (500) | 70 | ** |
| Exatract in Preparation Example 7 | 88.0 | 114 (100) | 10 | |
| Exatract in Preparation Example 7 | 88.0 | 227 (200) | 40 | * |
| Exatract in Preparation Example 7 | 88.0 | 568 (500) | 70 | ** |

*[1]In Tables here in after, numerals in parentheses are contents of non-sugar only.

Example 4

Anti-Virus Effect by an Intake of the Less-Sugar Fraction

1) Tested Extracts

Total 10 extracts were tested: the powder of the extract prepared in Preparation Example 5, the powders of samples 1 to 8 prepared in Preparation Example 6 and the powder of desalinized extract prepared by ion chromatographic separation in Preparation Example 7.

2) Anti-Virus Test

S1c:ICR male mice of 5 week-old (about 30 g in body weight) were used in 10 mice per group.

Each of the aforesaid extract was dissolved or suspended in sterilized distilled water and orally, forcedly administered in an amount shown in Table 10 to the mice. The administration was performed 3 times in total, i.e., immediately after, one day after and two days after the inoculation of virus. To the control group of the mice, the same volume of sterilized distilled water was orally forcedly administered. A suspension of pig-origin Pseudorabies virus was subcutaneously inoculated to the mice in an amount of 0.2 ml which corresponded to 1 MLD (133 PFU/mouse). Seven days' survival ratio was determined. The results evaluated by $\chi^2$ test are as shown in Table 10.

The groups administered the sugar-cane-derived extract clearly showed higher survival ratios which increased with the increasing amount of the administration.

The extracts having a higher non-sugar content, i.e., the extract of Preparation Example 5, the extracts of samples 1 to 3 of Preparation Examples 6, and the extract of Preparation Example 7, showed particularly higher survival ratios. Therefore, sugar is not considered to be the present active ingredient.

TABLE 10

Infection Preventing Test against Virus

| Tested Extract | non-sugar content (%) | Administered amount of extract mg/kg (as non-sugar) | Survival ratio (%) | $\chi^2$ test |
|---|---|---|---|---|
| Control | | Sterilized water 0.5 ml | 0 | |
| Exatract in Preparation Example 5 | 91.8 | 109 (100) | 10 | |
| Exatract in Preparation Example 5 | 91.8 | 218 (200) | 40 | * |
| Exatract in Preparation Example 5 | 91.8 | 545 (500) | 80 | ** |
| Exatract sample 1 in Preparation Example 6 | 100.0 | 200 (200) | 40 | * |
| Exatract sample 1 in Preparation Example 6 | 100.0 | 500 (500) | 80 | ** |
| Exatract sample 2 in Preparation Example 6 | 100.0 | 200 (200) | 50 | * |
| Exatract sample 2 in Preparation Example 6 | 100.0 | 500 (500) | 90 | ** |
| Exatract sample 3 in Preparation Example 6 | 89.6 | 223 (200) | 30 | |
| Exatract sample 3 in Preparation Example 6 | 89.6 | 558 (500) | 80 | ** |
| Exatract sample 4 in Preparation Example 6 | 52.3 | 382 (200) | 20 | |
| Exatract sample 4 in Preparation Example 6 | 52.3 | 956 (500) | 60 | ** |

TABLE 10-continued

Infection Preventing Test against Virus

| Tested Extract | non-sugar content (%) | Administered amount of extract mg/kg (as non-sugar) | Survival ratio (%) | $\chi^2$ test |
|---|---|---|---|---|
| Exatract sample 5 in Preparation Example 6 | 31.6 | 1582 (500) | 50 | * |
| Exatract sample 6 in Preparation Example 6 | 19.5 | 2564 (500) | 40 | * |
| Exatract sample 7 in Preparation Example 6 | 16.6 | 3012 (500) | 40 | * |
| Exatract sample 8 in Preparation Example 6 | 61.2 | 327 (200) | 30 | |
| Exatract sample 8 in Preparation Example 6 | 61.2 | 817 (500) | 60 | ** |
| Exatract in Preparation Example 7 | 89.2 | 112 (100) | 20 | |
| Exatract in Preparation Example 7 | 89.2 | 224 (200) | 40 | * |
| Exatract in Preparation Example 7 | 89.2 | 561 (500) | 70 | ** |

Test Example 4

Fractions Separated with Sephadex G-25, Based on Molecular Weight, from the Extract Liquid Separated by Ion Chromatography and Bagasse Extract and Anti-Virus Effect Thereof Gel permeation chromatography was performed on the extract prepared in Preparation Example 3 (hot water extraction of bagasse) and the extract prepared in Preparation example 5 (liquid extract prepared by ion chromatography) for fractionation based on molecular weight.

The aforesaid extracts were pre-treated to prevent precipitates possibly present in the extract from clogging. The extract of Preparation Example 3 was diluted to a Brix of from 17.5 to 17.8 with distilled water and centrifuged at 600×g for 15 minutes to remove insoluble materials. The supernatant was suction filtered through a No. 2 filter paper, ex Advantec Toyo Co., or a glass fiber filter paper GA55, ex Advantec Toyo Co. The filtrate was subjected to gel permeation chromatography. The extract of Preparation Example 5 was diluted to a Brix of from 18.7 to 22.2 with distilled water and filtered through a glass fiber filter paper GA55, ex Advantec Toyo Co. The filtrate was subjected to gel permeation chromatography.

A column having an inner diameter of 26 mm and a height of 630 mm was packed with 315 ml of Sephadex G-25 Superfine, trade name of Amasham Pharmacia Biotech Co. FPLC system, ex Pharmacia Co was used for chromatography.

Figure 4:
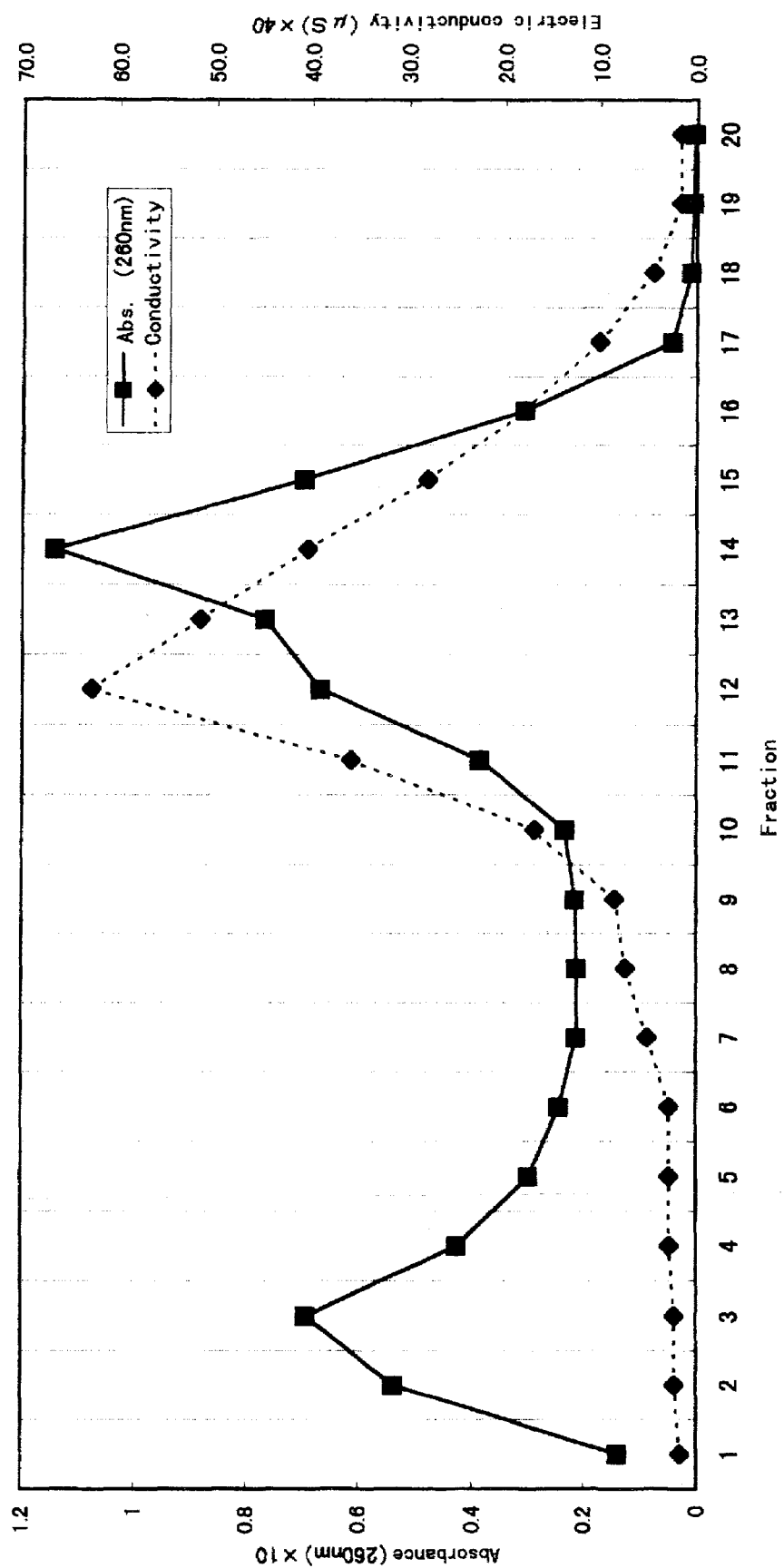
FIG. 4 shows an elution pattern obtained in gel permeation chromatography on the extract of Preparation Example 3, performed in Test Example 4.
Figure 5:
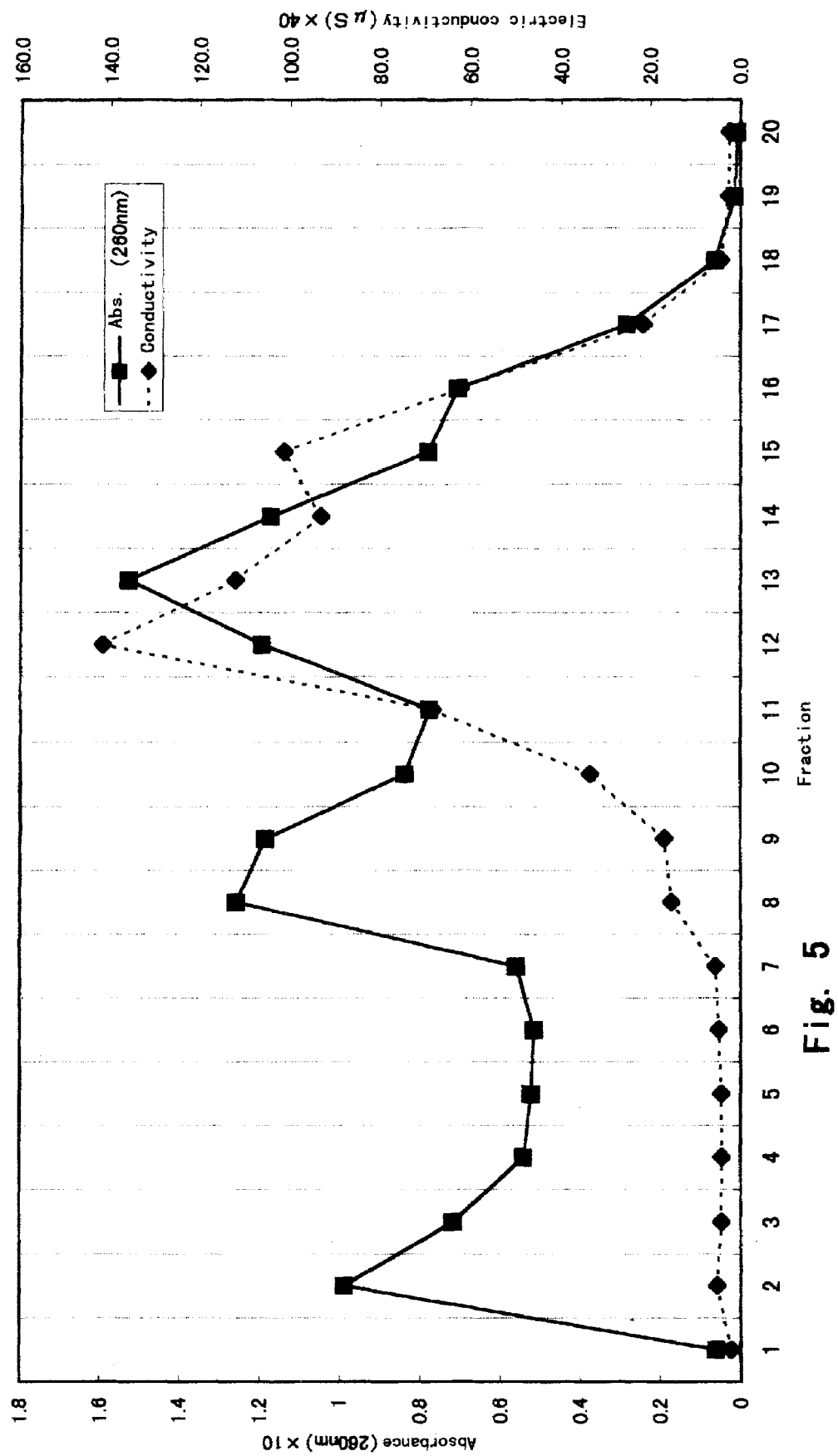
FIG. 5 shows an elution pattern obtained in gel permeation chromatography on the extract of Preparation Example 5, performed in Test Example 4.
Figure 6:
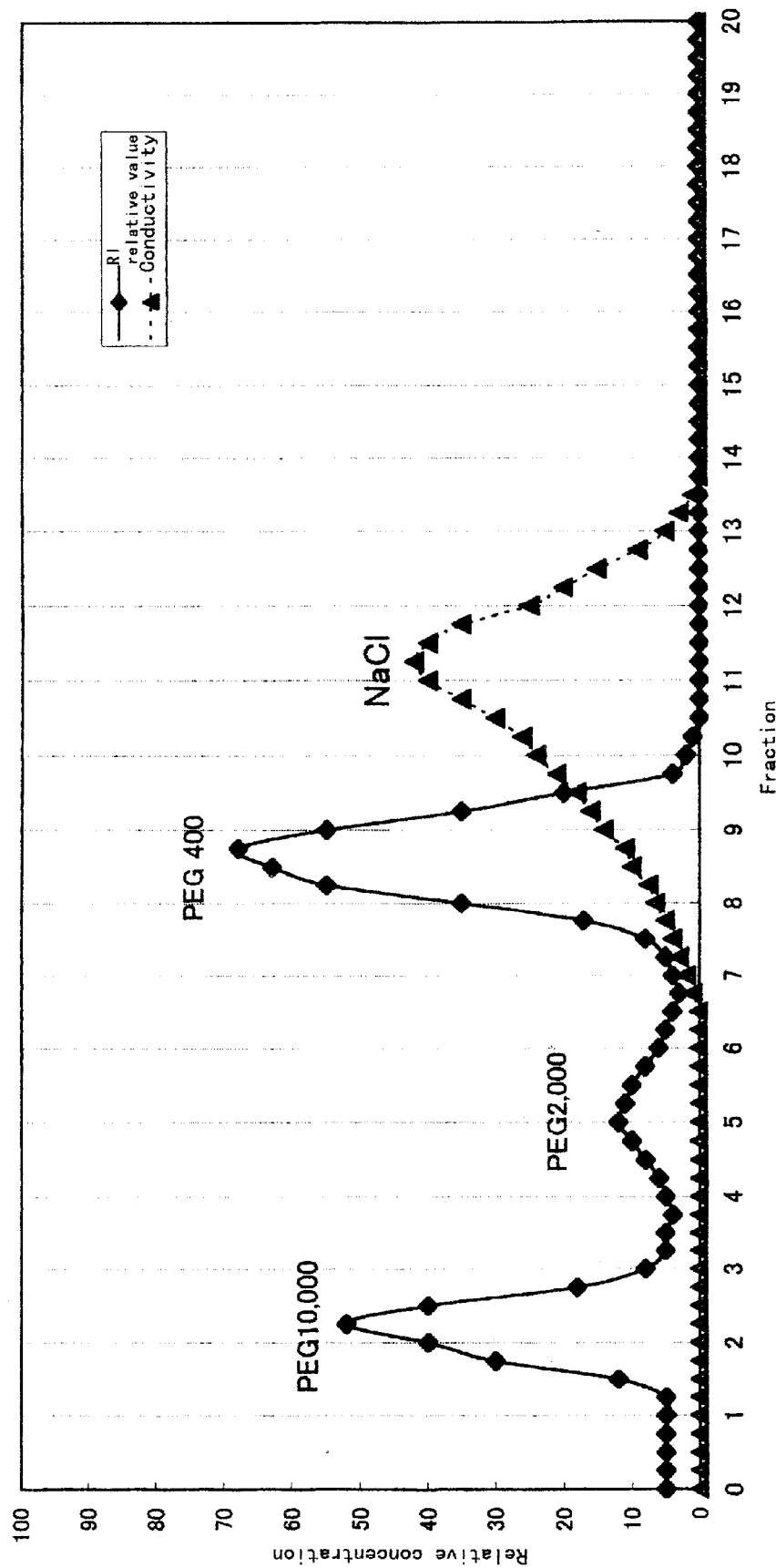
FIG. 6 shows an elution pattern obtained in gel permeation chromatography on molecular weight markers, performed in Test Example 4.

A degassed solution of ethanol/water=35/65 by volume was used as an eluent, which was passed through the column at a flow rate of SV=0.25 hr$^{-1}$ (1.32 ml/min) at a room temperature. For the extract of Preparation Example 3, a sample feeding amount was 6 ml when filtered with No. 2 filter paper, and 17 ml when filtered with the glass fiber filter paper. For the extract of Preparation Example 5, 6 ml was fed. The chromatography was repeated at least 5 times in the same conditions to confirm reproducibility in chromatogram. At about 80 minutes after the sample feeding was initiated, collection was started. One fractionation was collected over 15 minutes. A total of 20 fractions were collected from each of the extracts of Preparation Examples of 3 and 5. Chromatograms are as shown in FIGS. 4 and 5. FIG. 6 shows a chromatogram of a molecular weight marker in the same conditions.

The twenty fractions were combined into 3 samples: sample 1 consisting of fractions 1 to 4 containing substances with molecular weight of 10000 or more, sample 2 consisting of fractions 5 to 11 up to a front part of the peak in electric conductivity, and sample 3 consisting of fractions 12 to 20 containing much salts.

These samples 1 to 3 were freeze-dried to become powder. Analysis results are as shown in Table 11. Here, the definitions of a distribution ratio of freeze-dried solid content and saccharides contents are the same as those in Table 1. Using each of the powders, an anti-virus test was made in the same manner as in Example 4. The results are as shown in Table 12.

No significant differences among samples 1 to 3 were observed. From this, it is seen that there are a plurality of anti-virus active substances both in the extracts obtained by ion chromatographic separation and in the hot water extract of bagasse, which substances have a wide range of molecular weights.

TABLE 11

| | Distribution ratio of freeze-dried solid content (%) | Sucurose content (%) | Glucose content (%) | Fructose content (%) |
|---|---|---|---|---|
| Fractionated sample 1 in Preparation Example 3 | 8.8 | 0 | 0 | 0 |
| Fractionated sample 2 in Preparation Example 3 | 42.3 | 20.7 | 3.5 | 3.1 |
| Fractionated sample 3 in Preparation Example 3 | 48.9 | 0 | 0 | 0 |
| Fractionated sample 1 in Preparation Example 5 | 46.5 | 0 | 0 | 0 |
| Fractionated sample 2 in Preparation Example 5 | 28.8 | 9.8 | 1.9 | 1.6 |
| Fractionated sample 3 in Preparation Example 5 | 24.8 | 0 | 0 | 0 |

TABLE 12

Infection Preventing Test against Virus

| Tested extract | Non-sugar content (%) | Administered amount of extract mg/kg (as non-sugar) | Survival ratio (%) | $\chi^2$ test |
|---|---|---|---|---|
| Control | | Sterilized water 0.5 ml | 0 | |
| Fractionated sample 1 in Preparation Example 3 | 100.0 | 200 (200) | 40 | * |
| Fractionated sample 1 in Preparation Example 3 | 100.0 | 500 (500) | 90 | ** |
| Fractionated sample 2 in Preparation Example 3 | 72.7 | 28 (20) | 30 | |
| Fractionated sample 2 in Preparation Example 3 | 72.7 | 688 (500) | 70 | ** |
| Fractionated sample 3 in Preparation Example 3 | 100.0 | 200 (200) | 30 | |
| Fractionated sample 3 in Preparation Example 3 | 100.0 | 500 (500) | 80 | ** |
| Fractionated sample 1 in Preparation Example 5 | 100.0 | 200 (200) | 50 | * |
| Fractionated sample 1 in Preparation Example 5 | 100.0 | 500 (500) | 90 | ** |
| Fractionated sample 2 in Preparation Example 5 | 86.7 | 231 (200) | 30 | |
| Fractionated sample 2 in Preparation Example 5 | 86.7 | 577 (500) | 70 | ** |
| Fractionated sample 3 in Preparation Example 5 | 100.0 | 200 (200) | 50 | * |
| Fractionated sample 3 in Preparation Example 5 | 100.0 | 500 (500) | 90 | ** |

Example 5

Evaluation of Effects of Vaccine Adjuvants

1) Tested Extracts

The following extracts were tested: the extract powder prepared by column chromatography in Preparation Example 1, the extract powder prepared from bagasse in Preparation Example 3, the extract powder prepared by ion chromatography in Preparation Example 5 and the extract powder prepared by desalinizing the extract obtained by ion chromatography in Preparation Example 7.

2) Evaluation of Effects of Vaccine Adjuvants

S1c:ICR mice of 5 week-old (male, about 30 g in body weight) were used in 10 mice per group.

Effects of vaccine adjuvants were tested in administration of the various sugar cane-derived extracts to the mice.

For the groups administered the extracts of Preparation Examples 1, 3, 5, and 7, commercially available pig-origin Pseudorabies virus vaccine (AWV) was diluted with a physiological saline solution about 20 times and 0.2 ml of the suspension was intramuscularly administered to the mice. Each extract powder in an amount of 500 mg less-sugar content/kg was dissolved in 0.5 ml of sterilized water. The extract solution was orally administered to the mice once per day for 6 days starting from the day of the vaccination. Fourteen days after the vaccination, 0.2 ml of a suspension of pig-origin Pseudorabies virus diluted with a physiological saline solution corresponding to 1 MLD was subcutaneously inoculated to the mice and 7 days' survival ratio was determined.

As to the extract of Preparation Example 3, additional group of mice was used where a mixture of the vaccine and a solution prepared by dissolving the extraction in an amount of 100mg less non-sugar content/kg in 0.5 ml of sterilized water was administered.

To the group without vaccination, 0.2 ml of a physiological saline solution instead of the vaccine and 0.5 ml of sterilized water instead of the extract were administered. To the group without administration of the extract, 0.5 ml of sterilized water was administered instead of the extract.

Effects of the adjuvant were evaluated by $\chi^2$ test against the survival ratio of the group without administration of the extract (with vaccine only was administered). The results are as shown in Table 13.

No significant difference was observed between the group without vaccine administration and the group without extract administration. The group where the mixture of the extract and the vaccine was intramuscularly administered showed no significant difference in a survival ratio. To the contrary, in the groups where the sugar cane-derived extracts were orally administered, significant increases in survival ratios were observed, which indicates that the present extract is effective as an vaccine adjuvant.

TABLE 13

Evaluation of Effects of Vaccine Adjuvants

| Tested extract | non-sugar content (%) | Administered amount of extract mg/kg (as non-sugar) | Administration method of extract | Immunity | Survival ratio (%) | $\chi^2$ test |
|---|---|---|---|---|---|---|
| No inoculation of vaccine | | Sterilized water 0.5 ml | Oral admistration | Physiological saline solution 0.2 m 1 im. | 0 | |
| No administration of extract | | Sterilized water 0.5 ml | Oral admistration | AWV 0.2 m 1 im. | 20 | |
| Exatract of Prep. Ex. 1 | 96.0 | 521 (500) | Oral admistration | AWV 0.2 m 1 im. | 80 | * |
| Exatract of Prep. Ex. 3 | 87.7 | 570 (500) | Oral admistration | AWV 0.2 m 1 im. | 80 | * |
| Exatract of Prep. Ex. 5 | 91.8 | 545 (500) | Oral admistration | AWV 0.2 m 1 im. | 80 | * |
| Exatract of Prep. Ex. 7 | 89.2 | 561 (500) | Oral admistraion | AWV 0.2 m 1 im. | 70 | * |
| Exatract of Prep. Ex. 3 | 87.7 | 114 (100) | Intramuscular administration*[1] | AWV 0.2 m 1 im. | 20 | |

*[1]Mixture with vaccine was admistered.
AWV: Pseudorabies virus vaccine.
im.: Intramuscular administeration
*: $0.01 < p \leq 0.05$

Example 6

1) Tested Extracts

The following extracts were tested; the extract powder prepared in Preparation Examples 1 to 4 and the extract powders of Preparation Example 2 processed in the same manner as in Example 2, i.e., the fraction with a molecular weight of 1000 or smaller, and the fraction with a molecular weight larger than 1000.

2) Anti-Endotoxin Effect

Slc:ICR male mice of 5 week-old (about 30 g in body weight) were used in 10 mice per group.

The extracts of Preparation Examples 1 to 4 and the processed extract of Preparation Example 2 were each dissolved or suspended in sterilized distilled water and orally administered to the mice in an amount of 100 mg/kg twice, one day before and 6 hours after injection of endotoxin, lipopolysaccharide, referred to as LPS hereinafter. To the control group of mice, the same volume of sterilized distilled water was orally administered. *E. coli*-origin LPS was injected to a caudal vein of the mice in an amount of 0.2 ml corresponding to the minimum lethal dosage for attack by endotoxin. Four days' survival ratio was determined and evaluated by $\chi^2$ test. The results are as shown in Table 14.

TABLE 14

Evaluation of Anti-endotoxin Shock Effect

| Tested extract | Survival ratio (%) | $\chi^2$ test |
|---|---|---|
| Control | 0 | |
| Exatract in Preparation Example 1 | 50 | * |
| Exatract in Preparation Example 2 | 40 | * |
| Exatract in Preparation Example 3 | 40 | * |
| Exatract in Preparation Example 2 (Mw < 1000) | 60 | ** |
| Exatract in Preparation Example 2 (Mw >= 1000) | 20 | |

* $p < 0.05$,
** $p < 0.01$

The group administered the sugar cane-derived extract showed significantly higher survival ratios, which indicates that the present extract has an anti-endotoxin effect. For the processed extracts from Preparation Example 2, the lower molecular weight fraction had an higher effect than the higher molecular weight fraction.

Example 7

Anti-Endotoxin Effect

1) Tested Extracts

The powder extract prepared by ion chromatographic separation in Preparation Example 5 and the powder extract desalinized by ion chromatographic separation in Preparation Example 7 were tested.

2) Anti-Endotoxin Effect

Slc:ICR male mice of 5 week-old (about 30 g in body weight) were used in 10 mice per group.

Each of the extracts was dissolved or suspended in sterilized distilled water and orally administered to the mice in an amount of 100 mg/kg twice, on the day before and 6 hours after injection of endotoxin (LPS). To the control group of mice, the same volume of sterilized distilled water was orally administered. *E. coli*-origin LPS was injected to a caudal vein of the mice in an amount of 0.2 ml corresponding to the minimum lethal dosage for attack by endotoxin. Four days' survival ratio was determined and evaluated by $\chi^2$ test. The results are as shown in Table 15.

TABLE 15

Evaluation of Anti-endotoxin Shock Effect

| Tested extract | Non-sugar content (%) | Amount of administered extract (mg/kg) | Survival ratio (%) | $\chi^2$ test |
|---|---|---|---|---|
| Control | | | 0 | |
| Exatract in Prep. Example 5 | 91.8 | 100 | 50 | * |
| Exatract in Prep. Example 7 | 89.2 | 100 | 40 | * |

Example 8

S1c:ICR male mice of 3 week-old (about 12 g in body weight) were used in 5 mice per group. Group 1 for control was fed with MF standard feed and groups 2 to 5 were fed with MF standard feed added 0.1% of one of the extracts of Preparation Examples 1 to 4. At the end of 28 days feeding, a body weight was measured. Also, blood was collected and plasma was subjected to biochemical analyses. The results of weight increase are as shown in Table 16 and those of the biochemical analyses are as shown in Table 17.

In Table 16, "weight increase" means weight gain in the test period; "weight increase ratio" means a ratio of the weight increase to the weight (g) at the beginning of the test; and "ratio of the weight increase ratio" is percent of the weight increase ratio to the weight increase ratio that of the control group.

TABLE 16

Growth Promoting Effect of Exatract

| Test group | Weight increase (g) | Weight increase ratio | Ratio of weight increase ratio (%) |
|---|---|---|---|
| Control | 27.6 | 2.29 | 100 |
| Exatract in Prep. Example 1 | 31.4 | 2.60 | 114 |
| Exatract in Prep. Example 2 | 30.9 | 2.55 | 111 |
| Exatract in Prep. Example 3 | 30.0 | 2.51 | 110 |
| Exatract in Prep. Example 4 | 29.9 | 2.48 | 108 |

The groups where the sugar cane-derived extract was fed showed significant increase in weight, which indicates a growth promotion effect of the present extract. No abnormality was detected in the biochemical analyses.

Example 9

Growth Promoting Effect of the Extracts from Preparation Examples 3, 5 and 7

S1c:ICR male mice of 3 week-old (about 12 g in body weight) were used in 5 mice per group. A dosage of non-sugar portion was made constant, because sugar was not considered to be active ingredient. A control group was fed with MF standard feed and test groups were freely given MF standard feed mixed with 0.1% (as non-sugar content) of one of the extracts from Preparation Example 3 (bagasse extract), Example 5(extract separated by ion chromatography) and Example 7 (extract separated by ion chromatography and desalinized. At the end of 28 days feeding, a body weight was measured. Also, blood was collected and plasma was subjected to biochemical analyses. The results of weight increase are as shown in Table 18 and those of the biochemical analyses are as shown in Table 19.

In Table 18, "weight increase" means weight gain in the test period; "weight increase ratio" means a ratio of the weight increase to the weight (g) at the beginning of the test; and "ratio of the weight increase ratio" is percent of the weight increase ratio to the weight increase ratio that of the control group.

TABLE 18

Growth Promoting Effect of Extract

| Test group | Weight increase (g) | Weight increase ratio | Ratio of weight increase ratio (%) |
|---|---|---|---|
| Control | 27.1 | 2.34 | 100 |
| 1.00% Addition of extract in Preparation Example 3 | 29.3 | 2.54 | 109 |

TABLE 17

Biochemical Analyses Results of Plasma after Administration of Extract

| | Analysis item | | | | | |
|---|---|---|---|---|---|---|
| Test group | GPT (IU/L) | GOT (IU/L) | ALP (IU/L) | GLU (mg/dl) | CRNN (mg/dl) | T.CHO (mg/dl) |
| Control | 35.4 ± 49.8 | 50.8 ± 42.1 | 205.8 ± 23.3 | 156.0 ± 13.2 | 0.162 ± 0.028 | 114.6 ± 13.8 |
| Extract in Prep. Exmple 1 | 22.0 ± 10.5 | 46.0 ± 6.8 | 190.0 ± 39.0 | 179.0 ± 25.0 | 0.112 ± 0.031 | 114.8 ± 15.3 |
| Extract in Prep. Exmple 2 | 31.0 ± 21.8 | 48.0 ± 9.7 | 186.6 ± 28.8 | 181.2 ± 21.9 | 0.134 ± 0.029 | 115.4 ± 13.4 |
| Extract in Prep. Exmple 3 | 16.4 ± 4.4 | 37.0 ± 8.8 | 172.2 ± 20.8 | 170.8 ± 10.0 | 0.116 ± 0.010 | 103.8 ± 15.8 |
| Extract in Prep. Exmple 4 | 18.6 ± 4.5 | 53.8 ± 23.3 | 220.4 ± 35.5 | 190.0 ± 24.4 | 0.120 ± 0.032 | 110.0 ± 12.6 |

| | Analysis item | | | | |
|---|---|---|---|---|---|
| Test group | TG (mg/dl) | T.PRO (g/dl) | PL (mg/dl) | ALB-U (g/dl) | LDH (IU/L) |
| Control | 91.6 ± 46.1 | 4.22 ± 0.34 | 225.2 ± 27.3 | 2.44 ± 0.20 | 962 ± 993 |
| Extract in Prep. Exmple 1 | 112.8 ± 35.0 | 4.42 ± 0.17 | 220.6 ± 20.7 | 2.56 ± 0.10 | 968 ± 259 |
| Extract in Prep. Exmple 2 | 90.4 ± 25.4 | 4.40 ± 0.27 | 218.2 ± 17.9 | 2.54 ± 0.22 | 1113 ± 277 |
| Extract in Prep. Exmple 3 | 88.8 ± 19.4 | 4.04 ± 0.08 | 202.2 ± 15.9 | 2.40 ± 0.00 | 767 ± 204 |
| Extract in Prep. Exmple 4 | 81.2 ± 33.5 | 3.88 ± 0.16 | 202.1 ± 17.9 | 2.26 ± 0.10 | 1420 ± 747 |

TABLE 18-continued

Growth Promoting Effect of Extract

| Test group | Weight increase (g) | Weight increase ratio | Ratio of weight increase ratio (%) |
|---|---|---|---|
| (0.1% addition as non-sugar components) 0.109% Addition of extract in Preparation Example 5 (0.1% addition as non-sugar components) | 29.5 | 2.52 | 108 |
| 0.114% Addition of extract in Preparation Example 7 (0.1% addition as non-sugar components) | 28.9 | 2.49 | 106 |

TABLE 19

Biological Analyses Results of Plasma after Administration of Exatract

| | Analysis item | | | | | |
|---|---|---|---|---|---|---|
| Test group | GPT (IU/L) | GOT (IU/L) | ALP (IU/L) | GLU (mg/dl) | CRNN (mg/dl) | T.CHO (mg/dl) |
| Control | 25.8 ± 5.7 | 53.6 ± 14.8 | 175.6 ± 90.7 | 164.8 ± 33.5 | 0.114 ± 0.021 | 116.2 ± 11.2 |
| Addition of Extract in Prep. Exmple 3 | 28.4 ± 5.2 | 55.2 ± 14.8 | 194.6 ± 23.8 | 215.8 ± 36.6 | 0.132 ± 0.024 | 102.4 ± 12.1 |
| Addition of Extract in Prep. Exmple 5 | 91.6 ± 9.2 | 52.2 ± 13.8 | 186.4 ± 38.1 | 161.2 ± 29.8 | 0.132 ± 0.029 | 90.0 ± 15.9 |
| Addition of Extract in Prep. Exmple 7 | 30.2 ± 6.3 | 61.6 ± 16.1 | 192.8 ± 14.6 | 210.0 ± 17.8 | 0.142 ± 0.040 | 98.8 ± 8.4 |

| | Analysis item | | | | |
|---|---|---|---|---|---|
| Test group | TG (mg/dl) | T.PRO (g/dl) | PL (mg/dl) | ALB-U (g/dl) | LDH (IU/L) |
| Control | 113.8 ± 42.6 | 4.36 ± 0.24 | 218.0 ± 16.5 | 2.46 ± 0.10 | 973.0 ± 500 |
| Addition of Extract in Prep. Exmple 3 | 36.2 ± 13.1 | 4.18 ± 0.07 | 197.0 ± 9.5 | 2.50 ± 0.11 | 456.0 ± 44.4 |
| Addition of Extract in Prep. Exmple 5 | 81.2 ± 42.4 | 4.18 ± 0.34 | 179.6 ± 30.2 | 2.34 ± 0.22 | 956 ± 135 |
| Addition of Extract in Prep. Exmple 7 | 44.0 ± 21.7 | 4.34 ± 0.10 | 208.2 ± 12.2 | 2.62 ± 0.07 | 849 ± 326 |

INDUSTRIAL APPLICABILITY

By administrating the present sugar cane-derived extract to man or animals orally, infection by bacteria or viruses for example can be prevented or remedied. In addition, diseases caused by endotoxin can be prevented or remedied.

The present sugar cane-derived extract works as an vaccine adjuvant and also promotes growth when administered orally, for example, to man or animals. The sugar cane-derived extract is plant-origin and a natural product which has been taken in by man from ancient times as non-centrifugal sugar such as brown sugar (KOKUTOU) and, accordingly, is safe to human or animal health. Also, the extract can be produced in low costs. The present extract is a natural product, but has a high preventive or remedial effect, an anti-endotoxin effect, a vaccine adjuvant effect, and a growth promoting effect even in a small dosage.

What is claimed is:

1. A method for enhancing antigenicity of a vaccine when administered to a man or animal, comprising the step of administering to a man or animal a vaccine adjuvant before, concurrently with, or after administration of the vaccine, wherein the vaccine adjuvant comprises a sugar cane-derived extract as an active ingredient; the sugar cane-derived extract contains a lower saccharide concentration than a sugar cane raw material selected from the group consisting of sugar cane juice, a liquid extract from sugar cane, and sugar cane-derived molasses; the sugar cane extract is present in said vaccine adjuvant in an amount effective to enhance antigenicity of said vaccine; and the sugar cane-derived extract is a fraction which absorbs light of a wavelength of 420 nm and is obtained by column chromatographic treatment utilizing differences in affinity to a fixed carrier which is an ion exchange resin packed in a column.

2. The method according to claim 1, wherein the ion exchange resin is a cation exchange resin.

3. The method according to claim 2, wherein the cation exchange resin is a strongly acidic cation exchange resin.

4. The method according to claim 3, wherein the strongly acidic cation exchange resin is of a sodium ion form or a potassium ion form.

5. The method according to claim 1, wherein the ion exchange resin is a gel form resin.

6. The method according to claim 5, wherein ion exchange chromatographic separation is carried out using a pseudo moving-bed continuous separation method.

7. The method according to claim 5, wherein the fraction absorbing light of a wavelength of 420 nm is further treated by electrodialysis to thereby decrease amounts of salts contained in said fraction.

8. The method according to claim 1, wherein ion exchange chromatographic separation is carried out using a pseudo moving-bed continuous separation method.

9. The method according to claim 8, wherein the fraction absorbing light of a wavelength of 420 nm is further treated by electrodialysis to thereby decrease amounts of salts contained in said fraction.

10. The method according to claim 1, wherein the fraction absorbing light of a wavelength of 420 nm is further treated by electrodialysis to thereby decrease amounts of salts contained in said fraction.

11. The method according to claim 1, wherein the sugar cane-derived extract comprises a component having a molecular weight of less than 1000.

12. The method according to claim 1, wherein the vaccine adjuvant is administered in the form of a food which comprises the sugar cane-derived extract.

13. The method according to claim 12, wherein the food is an animal feed.

* * * * *